(12) United States Patent
Leow et al.

(10) Patent No.: US 11,634,483 B2
(45) Date of Patent: Apr. 25, 2023

(54) NUCLEIC ACIDS ENCODING ANTI-VEGF-A ANTIBODIES AND USES THEREOF

(71) Applicant: MEDIMMUNE LIMITED, Cambridge (GB)

(72) Inventors: Ching Ching Leow, Gaithersburg, MD (US); Nazzareno Dimasi, Gaithersburg, MD (US); Karen Coffman, Gaithersburg, MD (US); Ping Tsui, Gaithersburg, MD (US); Changshou Gao, Gaithersburg, MD (US); Mario A. Cepeda, Winchester, MA (US); Adrian Schwartz Mittelman, Brookfield, CT (US)

(73) Assignee: MEDIMMUNE LIMITED, Cambridge (GB)

( * ) Notice: Subject to any disclaimer, the term of this patent is extended or adjusted under 35 U.S.C. 154(b) by 241 days.

(21) Appl. No.: 17/152,409

(22) Filed: Jan. 19, 2021

(65) Prior Publication Data

US 2021/0147531 A1    May 20, 2021

Related U.S. Application Data

(62) Division of application No. 16/327,362, filed as application No. PCT/EP2017/071106 on Aug. 22, 2017, now Pat. No. 10,919,958.

(60) Provisional application No. 62/378,391, filed on Aug. 23, 2016.

(51) Int. Cl.
C07K 16/22    (2006.01)
C12N 15/13    (2006.01)

(52) U.S. Cl.
CPC .......... *C07K 16/22* (2013.01); *C07K 2317/21* (2013.01); *C07K 2317/33* (2013.01); *C07K 2317/565* (2013.01); *C07K 2317/92* (2013.01)

(58) Field of Classification Search
None
See application file for complete search history.

(56) References Cited

U.S. PATENT DOCUMENTS

2011/0177074 A1    7/2011    Sivakumar et al.

FOREIGN PATENT DOCUMENTS

| CN | 1259962 A | 7/2000 |
|----|-----------|--------|
| CN | 102006885 A | 4/2011 |
| CN | 102276722 A | 12/2011 |
| CN | 103562222 A | 2/2014 |
| WO | WO-98/45331 A2 | 10/1998 |
| WO | WO-2009/120922 A2 | 10/2009 |
| WO | WO-2010/124009 A2 | 10/2010 |

OTHER PUBLICATIONS

Chen et al., "Selection and analysis of an optimized anti-VEGF antibody: crystal structure of an affinity-matured fab in complex with antigen," Journal of Molecular Biology, vol. 293, No. 4, Nov. 1999 (Nov. 5, 1999), pp. 865-881.
Chengzhong Cai et al, "Differential Expression of VEGF 121, VEGF 165 and VEGF 189 in Angiomas and Squamous Cell Carcinoma Cell Lines of the Head Neck," Anticancer Research, vol. 30, Mar. 1, 2010, pp. 805-810.
International Search Report and Written Opinion in International Application No. PCT/EP2017/071106, dated Sep. 9, 2017.
Klaus Podar et al, "The pathophysiologic role of VEGF in hematologic malignancies: therapeutic implications," Blood, vol. 105. Oct. 7, 2004, pp. 1383-1395.
Mohamed Muhsin et al: "Fresh from the Pipeline: Bevacizumab," Nature Reviews. Drug Discovery,vol. 3, No. 12, Dec. 2004, pp. 995-996.
Rudikoff et al., "Single amino acid substitution altering antigen-binding specificity," Proceedings of the National Academy of Sciences, vol. 79, No. 6, Mar. 1, 1982 (Mar. 1, 1982), pp. 1979-1983.
Stephan Duebel, "Handbook of Therapeutic Antibodies, Chapter 6," Jan. 1, 2007, Handbook of Therapeutic Antibo, Wiley-VCH, Weinheim. pp. 119-144.
Tarallo et al., "The vascular endothelial growth factors and receptors family: Up to now the only target for anti-angiogenesis therapy," International Journal of Biochemistry and Cell Biology, vol. 64, May 1, 2015 (May 1, 2015), pp. 185-189.
Ferrara et al., Bevacizumab (Avastin), a humanized anti-VEGF monoclonal antibody for cancer therapy, Biochemical and Biophysical Research Communications, 2005, vol. 333, No. 2, pp. 328-335, 8 pages.
Li et al., Progress in Anti-tumor Angiogenesis Drugs Targeting VEGF/VEGFR, Progress in Modern Biomedicine, 2014, vol. 14, No. 16, pp. 3158-3162, 5 pages.
Lin et al., "Identification of a Neutralizing ScFv Binding to Human Vascular Endothelial Growth Factor 165 (VEGF165) Using a Phage Display Antibody Library," Appl Biochem Biotechnol (2008) vol. 144, pp. 15-26.
Woolard Jeanette et al.: "Molecular Diversity of VEGF-A as a Regulator of Its Biological Activity", Microcirculation, vol. 16, No. 7, Jan. 1, 2009 (Jan. 1, 2009), pp. 572-592, XP055804213, US ISSN: 1073-9688, DOI: 10.1080/10739680902997333.
Xuan et al., Research progresses in anti-tumor effects of drugs inhibiting tumor angiogenesis, Chinese Journal of New Drugs, 2014, vol. 23, No. 3, pp. 282-288, 7 pages.

*Primary Examiner* — Christine J Saoud
*Assistant Examiner* — Jon M Lockard
(74) *Attorney, Agent, or Firm* — Foley & Lardner LLP

(57) ABSTRACT

The present invention relates to antibodies having activity against a vascular endothelial growth factor (VEGF), and methods of making and using such antibodies.

4 Claims, 9 Drawing Sheets

Specification includes a Sequence Listing.

Figure 3

```
VH      <--------FWR1----------> <CDR1> <------FWR2----> <-----CDR2------> <-----------FWR3----------->
E06     EVQLLESGGGLVQPGGSLRLSCAASGFTFS WYEMY WVRQAPGKGLEWVS SISPSGGWTMYADSVKG RFTISRDNSKNTLYLQMNSLRAEDTAVYYCAT 98   SEQ ID NO: 119
VH3-23*2 ............................. S.A.S ................ A..G....S.Y. ................................      SEQ ID NO: 120

VL      <--------FWR1---------> <---CDR1------> <-----FWR2------> <-CDR2-> <-----------FWR3----------->
E06     DIQMTQSPATLSLSPGERATLSC RASQSVSSSYLA WYQQKPGQAPRLLIY GASSRAT GIPDRFSGSGSGTDFTLTISRLEPEDFATYYC QQSYSTFS 97   SEQ ID NO: 121
VK3-NL5 E.VL................... ............ ............... D...... ................................ V... ..-----  SEQ ID NO: 122
```

A)

B)

(-) H1RK (+) H1RK

NUCLEIC ACIDS ENCODING ANTI-VEGF-A ANTIBODIES AND USES THEREOF

CROSS-REFERENCE TO RELATED APPLICATIONS

This application is a divisional application of U.S. patent application Ser. No. 16/327,362, filed on Feb. 22, 2019, which is a U.S. National Stage application of International Application No. PCT/EP2017/071106, filed on Aug. 22, 2017, which claims benefit under 35 U.S.C. § 119(e) of the U.S. Provisional Application No. 62/378,391, filed on Aug. 23, 2016. Each of the above listed applications is incorporated by reference herein in its entirety for all purposes.

REFERENCE TO THE SEQUENCE LISTING

This application incorporates by reference a Sequence Listing submitted with this application as text file entitled 106105-0512_SL.txt, created on Sep. 10, 2020, and having a size of 117,266 bytes.

FIELD OF THE INVENTION

The invention relates to antibodies having activity against vascular endothelial growth factor (VEGF) and uses of such antibodies.

BACKGROUND TO THE INVENTION

Angiogenesis, the formation of new blood vessels from existing vasculature, is a complex biological process required for the formation and physiological functions of virtually all the organs. It is an essential element of embryogenesis, normal physiological growth, repair and pathological processes such as tumour expansion. Normally, angiogenesis is tightly regulated by the local balance of angiogenic and angiostatic factors in a multi-step process involving vessel sprouting, branching and tubule formation by endothelial cells (involving processes such as activation of endothelial cells (ECs), vessel destabilisation, synthesis and release of degradative enzymes, EC migration, EC proliferation, EC organisation and differentiation and vessel maturation).

In the adult, physiological angiogenesis is largely confined to wound healing and several components of female reproductive function and embryonic development. In disease-related angiogenesis which includes any abnormal, undesirable or pathological angiogenesis, the local balance between angiogenic and angiostatic factors is dysregulated leading to inappropriate and/or structurally abnormal blood vessel formation. Pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacology. Science. 16: 57-66; Folkman, 1995, Nature Medicine 1: 27-31). In cancer, growth of primary and secondary tumours beyond 1-2 mm3 requires angiogenesis (Folkman, J. New England Journal of Medicine 1995; 33, 1757-1763).

VEGF is a potent and ubiquitous vascular growth factor. Prior to identification of the role of VEGF as a secreted mitogen for endothelial cells, it was identified as a vascular permeability factor, highlighting VEGF's ability to control many distinct aspects of endothelial cell behaviour, including proliferation, migration, specialization and survival (Ruhrberg, 2003 BioEssays 25:1052-1060). VEGF-A was the first member of the VEGF family of structurally related dimeric glycoproteins belonging to the platelet-derived growth factor superfamily to be identified. Beside the founding member, VEGF-A, the VEGF family includes VEGF-B, VEGF-C, VEGF-D, VEGF-E, placental growth factor (PIGF) and endocrine gland-derived VEGF (EG-VEGF). Active forms of VEGF are synthesised either as homodimers or heterodimers with other VEGF family members. Human VEGF-A exists in six isoforms generated by alternative splicing: VEGF121, VEGF145, VEGF165, VEGF183, VEGF189 and VEGF206. These isoforms differ primarily in their bioavailability, with VEGF165 being the predominant isoform (Podar, et al. 2005 Blood 105(4):1383-1395) but with the others also having biological activity. The regulation of splicing during embryogenesis to produce stage- and tissue-specific ratios of the various isoforms creates rich potential for distinct and context dependent behavior of endothelial cells in response to VEGF.

VEGF is believed to be an important stimulator of both normal and disease-related angiogenesis (Jakeman, et al. 1993 Endocrinology: 133,848-859; Kolch, et al. 1995 Breast Cancer Research and Treatment: 36,139-155) and vascular permeability (Connolly, et al. 1989 J. Biol. Chem: 264, 20017-20024). Antagonism of VEGF action by sequestration of VEGF with antibodies can result in reduction of tumor growth (Kim, et al. 1993 Nature: 362,841-844). Heterozygous disruption of the VEGF gene resulted in fatal deficiencies in vascularisation (Carmeliet, et al. 1996 Nature 380:435-439; Ferrara, et al. 1996 Nature 380:439-442).

There is at least one commercially marketed anti-VEGF-A antibody, which is Avastin®. However, there are serious, sometimes fatal, toxicities associated with its use, including non-gastrointestinal fistulas, thromboembolic events, hypertension, reversible posterior leukoencephalopathy syndrome, etc. As such, there is an unmet need at least as it relates to improving the safety associated with targeting VEGF-A. To this end, the antibodies of the invention have binding characteristics that support such an improvement over the art, including the ability of these antibodies to differentially bind VEGF-A isoforms.

SUMMARY OF THE INVENTION

The invention relates to binding molecules, including antibodies, that bind to VEGF-A. The invention further relates to binding molecules, including antibodies, that bind to one or more VEGF-A isoforms with greater affinity when compared to one or more other VEGF-A isoforms. The invention also relates to binding molecules, including antibodies, that bind to VEGF-A and reduce the activity of at least one biological activity of VEGF-A.

BRIEF DESCRIPTION OF THE DRAWINGS

FIG. 3. Sequence alignment of clone E06 and the most sequence homologous germline genes. Figure discloses SEQ ID NOS: 119-122, respectively, in order of appearance.

DETAILED DESCRIPTION

Definitions

Figure 1:
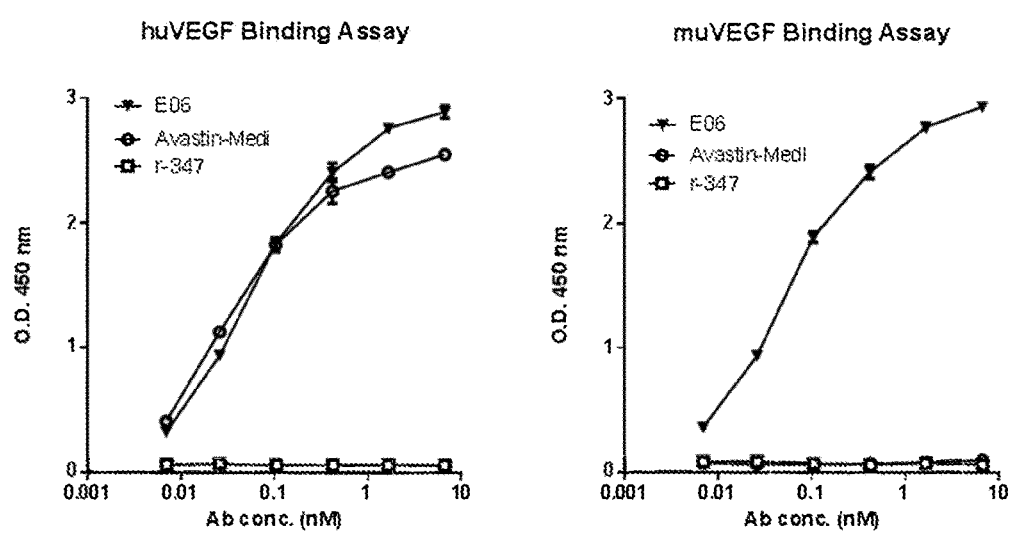
FIG. 1. Representative data demonstrating binding to human VEGF165 and mouse VEGF164.

Before describing the present invention in detail, it is to be understood that this invention is not limited to specific compositions or process steps, as such can vary. As used in this specification and the appended claims, the singular forms "a," "an" and "the" include plural referents unless the context clearly dictates otherwise. The terms "a" (or "an"), as well as the terms "one or more," and "at least one" can be used interchangeably herein. Further it is understood that wherever aspects are described herein with the language "comprising," otherwise analogous aspects described in terms of "consisting of" and/or "consisting essentially of" are also provided.

As used herein, the term "binding molecule" refers to a molecule that is capable of binding to a target molecule or antigen in a manner similar to that of an antibody binding to an antigen. Examples of binding molecules include full-length antibodies and antigen-binding fragments. Examples of "antigen-binding fragments" of an antibody include (i) a Fab fragment, a monovalent fragment that includes a VL, VH, CL and CH1 domain of an antibody; (ii) a F(ab')2 fragment, a bivalent fragment that includes two Fab fragments linked by a disulfide bridge at a hinge region; (iii) a Fd fragment that includes the VH and CH1 domains; (iv) a Fv fragment that includes VL and VH domains of a single arm of an antibody, (v) a dAb fragment (Ward et al., (1989) Nature 341:544-546), which includes a VH domain; and (vi) an isolated complementarity determining region (CDR). Antigen-binding fragments can be produced by recombinant DNA techniques, or by enzymatic or chemical cleavage of intact immunoglobulins. In one embodiment, the antigen-binding fragment includes a single chain antibody, including, for example, a "single-chain variable fragment" or "scFv." scFv refers to a fusion protein that includes at least one variable region of a heavy chain (VH) and at least one variable region of a light chain (VL) of an immunoglobulin. These single chain antibody fragments can be obtained using conventional techniques known to those with skill in the art. For example, the VH and VL domains of a Fv fragment, which are encoded by separate genes, can be joined, using recombinant methods, by a synthetic linker that enables them to be made as a single polypeptide chain in which the VH and VL regions pair to form a monovalent molecule (See, Bird et al. (1988) Science 242:423-426; and Huston et al. (1988) Proc. Natl. Acad. Sci. USA 85:5879-5883).

Complementarity determining regions (CDRs) are responsible for antibody binding to its antigen. CDRs are determined by a number of methods in the art (including Kabat (Kabat et al., Sequences of Proteins of Immunological Interest, 5th Ed. Public Health Service, National Institutes of Health, Bethesda, Md. (1991)); Chothia (Chothia and Lesk, J. Mol. Biol. 196:901-917 (1987)); IMGT (ImMunoGeneTics) (Lefranc, M. P. et al., Dev. Comp. Immunol. 27: 55-77 (2003)); and other methods). Although specific CDR sequences are mentioned and claimed herein, the invention also encompasses CDR sequences defined by any method known in the art.

As use herein, the term "subject" refers to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples.

Binding Molecules

A binding molecule can include a full length or intact antibody, an antibody fragment, including an antigen binding fragment, a human, humanized, post-translationally modified, chimeric or fusion antibody, immunoconjugate, or a functional fragment thereof.

Suitable immunoglobulin molecules or portions thereof of the invention (i.e., binding molecules) can be or are derived from any isotype (e.g., IgG, IgE, IgM, IgD, IgA and IgY), sub-isotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Immunoglobulin molecules can include light chains classified as either lambda chains or kappa chains based on the amino acid sequence of the light chain constant region.

Production of Binding Molecules

Recombinant DNA methods for producing and screening for polypeptides, such as the binding molecules described herein, are known in the art (e.g. U.S. Pat. No. 4,816,567). DNA encoding the binding molecules or fragments thereof, for example, DNA encoding a VH domain, a VL domain, an scFv, or combinations thereof can be inserted into a suitable expression vector, which can then be transfected into a suitable host cell, such as *E. coli* cells, simian COS cells, Chinese Hamster Ovary (CHO) cells, or myeloma cells that do not otherwise produce an antibody protein, to obtain the binding molecule.

Suitable expression vectors are known in the art. An expression vector can contain a polynucleotide that encodes an antibody linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains. The expression vector can be transferred to a host cell by conventional techniques and the transfected cells can be cultured by conventional techniques to produce the binding molecule.

Mammalian cell lines suitable as hosts for expression of recombinant antibodies are known in the art and include many immortalized cell lines available from the American Type Culture Collection, including but not limit to CHO cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the binding molecule. To this end, eukaryotic host cells which possess the cellular machinery for proper processing of the primary transcript, glycosylation, and phosphorylation of the gene product may be used. Such mammalian host cells include CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. Human cell lines developed by immortalizing human lymphocytes can be used to recombinantly produce monoclonal antibodies. The human cell line PER.C6®. (Crucell, Netherlands) can be used to recombinantly produce monoclonal antibodies. Additional cell lines which may be used as hosts for expression of recombinant antibodies include insect cells (e.g. Sf21/Sf9, Trichoplusia ni Bti-Tn5b1-4) or yeast cells (e.g. S. cerevisiae, Pichia, U.S. Pat. No. 7,326,681; etc.), plants cells (U.S. 20080066200); and chicken cells (WO2008142124).

Antibodies can be stably expressed in a cell line using methods known in the art. Stable expression can be used for long-term, high-yield production of recombinant proteins. For stable expression, host cells can be transformed with an appropriately engineered vector that includes expression control elements (e.g., promoter, enhancer, transcription terminators, polyadenylation sites, etc.), and a selectable marker gene. Following the introduction of the foreign DNA, cells are allowed to grow for 1-2 days in an enriched media, and are then switched to a selective media. The selectable marker in the recombinant plasmid confers resistance to the selection and allows cells that have stably integrated the plasmid into their chromosomes to grow and form foci which in turn can be cloned and expanded into cell lines. Methods for producing stable cell lines with a high yield are known in the art and reagents are generally available commercially. Transient expression can also be carried out by using methods known in the art. Transient transfection is a process in which the nucleic acid introduced into a cell does not integrate into the genome or chromosomal DNA of that cell and is maintained as an extra-chromosomal element in the cell (e.g., as an episome).

A cell line, either stable or transiently transfected, is maintained in cell culture medium and conditions known in the art resulting in the expression and production of the binding molecule. Cell culture media can be based on commercially available media formulations, including, for example, DMEM or Ham's F12. In addition, the cell culture media can be modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including cell culture growth medium which is formulated to promote cellular growth or cell culture production medium which is formulated to promote recombinant protein production. The terms nutrient, ingredient, and component are used interchangeably herein to refer to the constituents that make up a cell culture medium. Cell lines can be maintained using a fed batch method. As used herein, "fed batch method," refers to a method by which a cell culture is supplied with additional nutrients after first being incubated with a basal medium. For example, a fed batch method may include adding supplemental media according to a determined feeding schedule within a given time period. Thus, a "fed batch cell culture" refers to a cell culture wherein the cells, typically mammalian, and culture medium are supplied to the culturing vessel initially and additional culture nutrients are fed, continuously or in discrete increments, to the culture during culturing, with or without periodic cell and/or product harvest before termination of culture.

Cell culture media and the nutrients contained therein are known to one of skilled in the art. The cell culture medium may include a basal medium and at least one hydrolysate, e.g., soy-based hydrolysate, a yeast-based hydrolysate, or a combination of the two types of hydrolysates resulting in a modified basal medium. The additional nutrients may include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, α-Minimal Essential Medium (α-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the invention include BME Basal Medium (Gibco-Invitrogen; see also Eagle, H (1965) Proc. Soc. Exp. Biol. Med. 89, 36); Dulbecco's Modified Eagle Medium (DMEM, powder) (Gibco-Invitrogen (#31600); see also Dulbecco and Freeman (1959) Virology. 8:396; Smith et al. (1960) Virology. 12:185. Tissue Culture Standards Committee, In Vitro 6:2, 93); CMRL 1066 Medium (Gibco-Invitrogen (#11530); see also Parker et al. (1957) Special Publications, N.Y. Academy of Sciences, 5:303).

The basal medium may be serum-free, meaning that the medium contains no serum (e.g., fetal bovine serum (FBS), horse serum, goat serum, or any other animal-derived serum known to one skilled in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. The cell culture medium may contain a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. A modified basal medium may further contain glutamine, e.g, L-glutamine, and/or methotrexate.

Purification and Isolation

Once a binding molecule has been produced, it may be purified by methods known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the binding molecules of the invention may be fused to heterologous polypeptide sequences (referred to herein as "tags") to facilitate purification.

Uses

Binding molecules of the invention can be used in a number of ways. For example, antibodies of the invention can be used to bind to VEGF-A and thereby reduce at least one biological activity of VEGF-A. More particularly, the antibodies of the invention can be used to bind to VEGF-165 and thereby reduce at least one biological activity of VEGF-165, which may include a reduction in activation or phosphorylation of its receptor, a reduction in angiogenesis in connection with cellular dysregulation, a reduction in tumor growth, a reduction in tumor volume, and/or reduction in tumor growth and tumor volume.

Exemplary Embodiments

An embodiment of the invention relates to a binding molecule comprising heavy chain complementarity determining regions 1-3 (i.e., HCDR1, HCDR2, and HCDR3) and light chain complementarity determining regions 1-3 (i.e., LCDR1, LCDR2, and LCDR3) of an antibody described herein.

Another embodiment relates to a binding molecule comprising HCDR1, HCDR2, and HCDR3 and LCDR1, LCDR2, and LCDR3 of an antibody described herein, wherein the binding molecule binds VEGF165.

Another embodiment relates to a binding molecule comprising HCDR1, HCDR2, and HCDR3 and LCDR1, LCDR2, and LCDR3 of an antibody described herein, wherein the binding molecule binds VEGF165 with greater affinity compared to VEGF121.

Another embodiment relates to a binding molecule comprising HCDR1, HCDR2, and HCDR3 and LCDR1, LCDR2, and LCDR3 of an antibody described herein, wherein the binding molecule binds VEGF165 with greater affinity compared to VEGF189.

Another embodiment relates to a binding molecule comprising HCDR1, HCDR2, and HCDR3 and LCDR1, LCDR2, and LCDR3 of an antibody described herein, wherein the binding molecule binds VEGF165 with greater affinity compared to VEGF121 and VEGF189.

Another embodiment relates to a binding molecule comprising HCDR1, HCDR2, and HCDR3 and LCDR1, LCDR2, and LCDR3 of an antibody described herein, wherein the binding molecule reduces human VEGFR2 phosphorylation, murine VEGFR2 phosphorylation, or both human and murine VEGFR2 phosphorylation.

Another embodiment relates to a binding molecule comprising HCDR1, HCDR2, and HCDR3 and LCDR1, LCDR2, and LCDR3 of an antibody described herein, wherein the binding molecule reduces angiogenesis.

Another embodiment relates to a binding molecule comprising HCDR1, HCDR2, and HCDR3 and LCDR1, LCDR2, and LCDR3 of an antibody described herein, wherein the binding molecule reduces tumor growth, reduces tumor volume, or reduces tumor growth and tumor volume as a result of being provided to a subject having a tumor.

Another embodiment relates to a binding molecule comprising HCDR1, HCDR2, and HCDR3 and LCDR1, LCDR2, and LCDR3 of an antibody described herein, wherein the binding molecule has one or more or any combination of the characteristics described herein, including binding VEGF165, binding VEGF165 with greater affinity compared to VEGF121, binding VEGF165 with greater affinity compared to VEGF189, binding VEGF165 with greater affinity compared to VEGF121 and VEGF189, reducing human VEGFR2 phosphorylation, murine VEGFR2 phosphorylation, or both human and murine VEGFR2 phosphorylation, reducing angiogenesis, or reducing tumor growth, reducing tumor volume, or reducing tumor growth and tumor volume as a result of being provided to a subject having a tumor.

An embodiment of the invention relates to a binding molecule comprising a heavy chain variable domain comprising HCDR1, HCDR2, and HCDR3 and a light chain variable domain comprising LCDR1, LCDR2, and LCDR3 of an antibody described herein.

Another embodiment relates to a binding molecule comprising a heavy chain variable domain comprising HCDR1, HCDR2, and HCDR3 and a light chain variable domain comprising LCDR1, LCDR2, and LCDR3 of an antibody described herein, wherein the binding molecule binds VEGF165.

Another embodiment relates to a binding molecule comprising a heavy chain variable domain comprising HCDR1, HCDR2, and HCDR3 and a light chain variable domain comprising LCDR1, LCDR2, and LCDR3 of an antibody described herein, wherein the binding molecule binds VEGF165 with greater affinity compared to VEGF121.

Another embodiment relates to a binding molecule comprising a heavy chain variable domain comprising HCDR1, HCDR2, and HCDR3 and a light chain variable domain comprising LCDR1, LCDR2, and LCDR3 of an antibody described herein, wherein the binding molecule binds VEGF165 with greater affinity compared to VEGF189.

Another embodiment relates to a binding molecule comprising a heavy chain variable domain comprising HCDR1, HCDR2, and HCDR3 and a light chain variable domain comprising LCDR1, LCDR2, and LCDR3 of an antibody described herein, wherein the binding molecule binds VEGF165 with greater affinity compared to VEGF121 and VEGF189.

Another embodiment relates to a binding molecule comprising a heavy chain variable domain comprising HCDR1, HCDR2, and HCDR3 and a light chain variable domain comprising LCDR1, LCDR2, and LCDR3 of an antibody described herein, wherein the binding molecule reduces human VEGFR2 phosphorylation, murine VEGFR2 phosphorylation, or both human and murine VEGFR2 phosphorylation.

Another embodiment relates to a binding molecule comprising a heavy chain variable domain comprising HCDR1, HCDR2, and HCDR3 and comprising a light chain variable domain comprising LCDR1, LCDR2, and LCDR3 of an antibody described herein, wherein the binding molecule reduces angiogenesis.

Another embodiment relates to a binding molecule comprising a heavy chain variable domain comprising HCDR1, HCDR2, and HCDR3 and comprising a light chain variable domain comprising LCDR1, LCDR2, and LCDR3 of an antibody described herein, wherein the binding molecule reduces tumor growth, reduces tumor volume, or reduces tumor growth and tumor volume as a result of being provided to a subject having a tumor.

Another embodiment relates to a binding molecule comprising a heavy chain variable domain comprising HCDR1, HCDR2, and HCDR3 and comprising a light chain variable domain comprising LCDR1, LCDR2, and LCDR3 of an antibody described herein, wherein the binding molecule has one or more or any combination of the characteristics described herein, including binding VEGF165, binding VEGF165 with greater affinity compared to VEGF121, binding VEGF165 with greater affinity compared to VEGF189, binding VEGF165 with greater affinity compared to VEGF121 and VEGF189, reducing human VEGFR2 phosphorylation, murine VEGFR2 phosphorylation, or both human and murine VEGFR2 phosphorylation, reducing angiogenesis, or reducing tumor growth, reducing tumor volume, or reducing tumor growth and tumor volume as a result of being provided to a subject having a tumor.

An embodiment of the invention relates to a binding molecule comprising a full-length antibody comprising HCDR1, HCDR2, and HCDR3 and LCDR1, LCDR2, and LCDR3 of an antibody described herein.

Another embodiment relates to a binding molecule comprising a full-length antibody comprising HCDR1, HCDR2, and HCDR3 and LCDR1, LCDR2, and LCDR3 of an antibody described herein, wherein the binding molecule binds VEGF165.

Another embodiment relates to a binding molecule comprising a full-length antibody comprising HCDR1, HCDR2, and HCDR3 and LCDR1, LCDR2, and LCDR3 of an antibody described herein, wherein the binding molecule binds VEGF165 with greater affinity compared to VEGF121.

Another embodiment relates to a binding molecule comprising a full-length antibody comprising HCDR1, HCDR2, and HCDR3 and LCDR1, LCDR2, and LCDR3 of an antibody described herein, wherein the binding molecule binds VEGF165 with greater affinity compared to VEGF189.

Another embodiment relates to a binding molecule comprising a full-length antibody comprising HCDR1, HCDR2, and HCDR3 and LCDR1, LCDR2, and LCDR3 of an antibody described herein, wherein the binding molecule binds VEGF165 with greater affinity compared to VEGF121 and VEGF189.

Another embodiment relates to a binding molecule comprising a full-length antibody comprising HCDR1, HCDR2, and HCDR3 and LCDR1, LCDR2, and LCDR3 of an antibody described herein, wherein the binding molecule reduces human VEGFR2 phosphorylation, murine VEGFR2 phosphorylation, or both human and murine VEGFR2 phosphorylation.

Another embodiment relates to a binding molecule comprising a full-length antibody comprising HCDR1, HCDR2, and HCDR3 and LCDR1, LCDR2, and LCDR3 of an antibody described herein, wherein the binding molecule reduces angiogenesis.

Another embodiment relates to a binding molecule comprising a full-length antibody comprising HCDR1, HCDR2, and HCDR3 and LCDR1, LCDR2, and LCDR3 of an antibody described herein, wherein the binding molecule reduces tumor growth, reduces tumor volume, or reduces tumor growth and tumor volume as a result of being provided to a subject having a tumor.

Another embodiment relates to a binding molecule comprising a full-length antibody comprising HCDR1, HCDR2, and HCDR3 and LCDR1, LCDR2, and LCDR3 of an antibody described herein, wherein the binding molecule has one or more or any combination of the characteristics described herein, including binding VEGF165, binding VEGF165 with greater affinity compared to VEGF121, binding VEGF165 with greater affinity compared to VEGF189, binding VEGF165 with greater affinity compared to VEGF121 and VEGF189, reducing human VEGFR2 phosphorylation, murine VEGFR2 phosphorylation, or both human and murine VEGFR2 phosphorylation, reducing angiogenesis, or reducing tumor growth, reducing tumor volume, or reducing tumor growth and tumor volume as a result of being provided to a subject having a tumor.

An embodiment of the invention relates to a binding molecule comprising a full-length IgG1 antibody comprising HCDR1, HCDR2, and HCDR3 and LCDR1, LCDR2, and LCDR3 of an antibody described herein.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule binds VEGF165.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule binds VEGF165 with greater affinity compared to VEGF121.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule binds VEGF165 with greater affinity compared to VEGF189.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule binds VEGF165 with greater affinity compared to VEGF121 and VEGF189.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule reduces human VEGFR2 phosphorylation, murine VEGFR2 phosphorylation, or both human and murine VEGFR2 phosphorylation.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule reduces angiogenesis.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule reduces tumor growth, reduces tumor volume, or reduces tumor growth and tumor volume as a result of being provided to a subject having a tumor.

Another embodiment relates to a binding molecule comprising a full-length IgG1 antibody comprising HCDR1, HCDR2, and HCDR3 and LCDR1, LCDR2, and LCDR3 of an antibody described herein, wherein the binding molecule has one or more or any combination of the characteristics described herein, including binding VEGF165, binding VEGF165 with greater affinity compared to VEGF121, binding VEGF165 with greater affinity compared to VEGF189, binding VEGF165 with greater affinity compared to VEGF121 and VEGF189, reducing human VEGFR2 phosphorylation, murine VEGFR2 phosphorylation, or both human and murine VEGFR2 phosphorylation, reducing angiogenesis, or reducing tumor growth, reducing tumor volume, or reducing tumor growth and tumor volume as a result of being provided to a subject having a tumor.

An embodiment of the invention relates to a binding molecule which is a full-length antibody, including a full-length IgG1 antibody, comprising HCDR1, HCDR2, and HCDR3 and LCDR1, LCDR2, and LCDR3 of an antibody described herein.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule binds VEGF165.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule binds VEGF165 with greater affinity compared to VEGF121.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule binds VEGF165 with greater affinity compared to VEGF189.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule binds VEGF165 with greater affinity compared to VEGF121 and VEGF189.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule reduces human VEGFR2 phosphorylation, murine VEGFR2 phosphorylation, or both human and murine VEGFR2 phosphorylation.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule reduces angiogenesis.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule reduces tumor growth, reduces tumor volume, or reduces tumor growth and tumor volume as a result of being provided to a subject having a tumor.

Another embodiment relates to a binding molecule which is a full-length antibody, including a full-length IgG1 antibody, comprising HCDR1, HCDR2, and HCDR3 and LCDR1, LCDR2, and LCDR3 of an antibody described herein, wherein the binding molecule has one or more or any combination of the characteristics described herein, including binding VEGF165, binding VEGF165 with greater affinity compared to VEGF121, binding VEGF165 with greater affinity compared to VEGF189, binding VEGF165 with greater affinity compared to VEGF121 and VEGF189, reducing human VEGFR2 phosphorylation, murine VEGFR2 phosphorylation, or both human and murine VEGFR2 phosphorylation, reducing angiogenesis, or reducing tumor growth, reducing tumor volume, or reducing tumor growth and tumor volume as a result of being provided to a subject having a tumor.

In a specific embodiment, there is an antibody comprising an HCDR1, HCDR2, and HCDR3 and an LCDR1, LCDR2, and LCDR3, wherein HCDR1, HCDR2, and HCDR3 and LCDR1, LCDR2, and LCDR3 comprise SEQ ID NOs: 79-84, respectively.

In another specific embodiment, there is an antibody comprising a heavy chain and a light chain comprising SEQ ID NOs: 73 and 77, respectively.

In another specific embodiment, there is an antibody comprising a heavy chain amino acid sequence comprising SEQ ID NO: 71 and a light chain amino acid sequence comprising SEQ ID NO: 75.

In another specific embodiment, there is an antibody comprising an HCDR1, HCDR2, and HCDR3 and an LCDR1, LCDR2, and LCDR3, wherein HCDR1, HCDR2, and HCDR3 and LCDR1, LCDR2, and LCDR3 comprise SEQ ID NOs: 79-84, respectively, and wherein the antibody is a monoclonal antibody.

In another specific embodiment, there is a nucleic acid sequence comprising polynucleotides encoding an antibody comprising an HCDR1, HCDR2, and HCDR3 and an LCDR1, LCDR2, and LCDR3, wherein HCDR1, HCDR2, and HCDR3 and LCDR1, LCDR2, and LCDR3 comprise SEQ ID NOs: 79-84, respectively.

In another specific embodiment, there is a vector comprising polynucleotides encoding an antibody comprising an HCDR1, HCDR2, and HCDR3 and an LCDR1, LCDR2, and LCDR3, wherein HCDR1, HCDR2, and HCDR3 and LCDR1, LCDR2, and LCDR3 comprise SEQ ID NOs: 79-84, respectively.

In another specific embodiment, there is a cell comprising a vector comprising polynucleotides encoding an antibody comprising an HCDR1, HCDR2, and HCDR3 and an LCDR1, LCDR2, and LCDR3, wherein HCDR1, HCDR2, and HCDR3 and LCDR1, LCDR2, and LCDR3 comprise SEQ ID NOs: 79-84, respectively.

In another specific embodiment, there is a method of making an antibody comprising culturing a cell comprising a vector comprising polynucleotides encoding an antibody comprising an HCDR1, HCDR2, and HCDR3 and an LCDR1, LCDR2, and LCDR3, wherein HCDR1, HCDR2, and HCDR3 and LCDR1, LCDR2, and LCDR3 comprise SEQ ID NOs: 79-84, respectively.

In another specific embodiment, there is a method of reducing angiogenesis comprising providing an antibody to a subject wherein the antibody comprises an HCDR1, HCDR2, and HCDR3 and an LCDR1, LCDR2, and LCDR3, wherein HCDR1, HCDR2, and HCDR3 and LCDR1, LCDR2, and LCDR3 comprise SEQ ID NOs: 79-84, respectively.

Sequences

| SEQ ID NO | SEQUENCE | DESCRIPTION |
|---|---|---|
| 1 | EVQLLESGGGLVQPGGSLRLSCAASGFTFSWYEMYWVRQA PGKGLEWVSSISPSGGWTMYADSVKGRFTISRDNSKNTLYL QMNSLRAEDTAVYYCATPLYSSDGLSAGDIWGQGTMVTVS SASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTKNQV SLTCLVKGFYPSDIAVEWESNGQPENNYKTTPPVLDSDGSFF LYSKLTVDKSRWQQGNVFSCSVMHEALHNHYTQKSLSLSP GK | Amino acid sequence of the heavy chain of E06 |
| 2 | GAGGTGCAGCTGCTGGAGAGCGGCGGCGGCCTGG TGCAGCCCGGCGGCAGCCTGAGGCTGAGCTGCGCCGCCA GCGGCTTCACCTTCAGCTGGTACGAGATGTACTGGGTGA GGCAGGCCCCCGGCAAGGGCCTGGAGTGGGTGAGCAGCA TCAGCCCCAGCGGCGGCTGGACCATGTACGCCGACAGCG TGAAGGGCAGGTTCACCATCAGCAGGGACAACAGCAAGA ACACCCTGTACCTGCAGATGAACAGCCTGAGGGCCGAGG ACACCGCCGTGTACTACTGCGCCACCCCCCTGTACAGCAG CGACGGCCTGAGCGCCGGCGACATCTGGGGCCAGGGCAC CATGGTGACCGTGAGCAGCGCCAGCACCAAGGGCCCCAG CGTGTTCCCCCTGGCCCCCAGCAGCAAGAGCACCAGCGG CGGCACCGCCGCCCTGGGCTGCCTGGTGAAGGACTACTT CCCCGAGCCCGTGACCGTGAGCTGGAACAGCGGCGCCCT GACCAGCGGCGTGCACACCTTCCCCGCCGTGCTGCAGAG CAGCGGCCTGTACAGCCTGAGCAGCGTGGTGACCGTGCC CAGCAGCAGCCTGGGCACCCAGACCTACATCTGCAACGT GAACCACAAGCCCAGCAACACCAAGGTGGACAAGAGGG TGGAGCCCAAGAGCTGCGACAAGACCCACACCTGCCCCC CCTGCCCCGCCCCCGAGCTGCTGGGCGGCCCCAGCGTGTT CCTGTTCCCCCCCAAGCCCAAGGACACCCTGATGATCAGC AGGACCCCCGAGGTGACCTGCGTGGTGGTGGACGTGAGC CACGAGGACCCCGAGGTGAAGTTCAACTGGTACGTGGAC GGCGTGGAGGTGCACAACGCCAAGACCAAGCCCAGGGA GGAGCAGTACAACAGCACCTACAGGGTGGTGAGCGTGCT GACCGTGCTGCACCAGGACTGGCTGAACGGCAAGGAGTA CAAGTGCAAGGTGAGCAACAAGGCCCTGCCCGCCCCCAT CGAGAAGACCATCAGCAAGGCCAAGGGCCAGCCCAGGG AGCCCCAGGTGTACACCCTGCCCCCCAGCAGGGAGGAGA TGACCAAGAACCAGGTGAGCCTGACCTGCCTGGTGAAGG GCTTCTACCCCAGCGACATCGCCGTGGAGTGGGAGAGCA ACGGCCAGCCCGAGAACAACTACAAGACCACCCCCCCG TGCTGGACAGCGACGGCAGCTTCTTCCTGTACAGCAAGCT GACCGTGGACAAGAGCAGGTGGCAGCAGGGCAACGTGTT CAGCTGCAGCGTGATGCACGAGGCCCTGCACAACCACTA CACCCAGAAGAGCCTGAGCCTGAGCCCCGGCAAG | Nucleotide sequence of the heavy chain of E06 |
| 3 | EVQLLESGGGLVQPGGSLRLSCAASGFTFSWYEMYWVRQA PGKGLEWVSSISPSGGWTMYADSVKGRFTISRDNSKNTLYL QMNSLRAEDTAVYYCATPLYSSDGLSAGDIWGQGTMVTVS S | Amino acid sequence of the heavy chain variable domain of E06 |
| 4 | GAGGTGCAGCTGCTGGAGAGCGGCGGCGGCCTGGTGCAG CCCGGCGGCAGCCTGAGGCTGAGCTGCGCCGCCAGCGGC TTCACCTTCAGCTGGTACGAGATGTACTGGGTGAGGCAG GCCCCCGGCAAGGGCCTGGAGTGGGTGAGCAGCATCAGC CCCAGCGGCGGCTGGACCATGTACGCCGACAGCGTGAAG GGCAGGTTCACCATCAGCAGGGACAACAGCAAGAACACC CTGTACCTGCAGATGAACAGCCTGAGGGCCGAGGACACC GCCGTGTACTACTGCGCCACCCCCCTGTACAGCAGCGAC GGCCTGAGCGCCGGCGACATCTGGGGCCAGGGCACCATG GTGACCGTGAGCAGC | Nucleotide sequence of the heavy chain variable domain of E06 |
| 5 | DIQMTQSPATLSLSPGERATLSCRASQSVSSSYLAWYQQKP GQAPRLLIYGASSRATGIPDRFSGSGSGTDFTLTISRLEPEDF ATYYCQQSYSTPSFGQGTRLEITRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | Amino acid sequence of the light chain of E06 |

-continued

| SEQ ID NO | SEQUENCE | DESCRIPTION |
|---|---|---|
| 6 | GACATCCAGATGACCCAGAGCCCCGCCACCCTGA GCCTGAGCCCCGGCGAGAGGGCCACCCTGAGCTGCAGGG CCAGCCAGAGCGTGAGCAGCAGCTACCTGGCCTGGTACC AGCAGAAGCCCGGCCAGGCCCCCAGGCTGCTGATCTACG GCGCCAGCAGCAGGGCCACCGGCATCCCCGACAGGTTCA GCGGCAGCGGCAGCGGCACCGACTTCACCCTGACCATCA GCAGGCTGGAGCCCGAGGACTTCGCCACCTACTACTGCC AGCAGAGCTACAGCACCCCCAGCTTCGGCCAGGGCACCA GGCTGGAGATCACCAGGACCGTGGCCGCCCCCAGCGTGT TCATCTTCCCCCCCAGCGACGAGCAGCTGAAGAGCGGCA CCGCCAGCGTGGTGT GCCTGCTGAACAACTTCTACCCCAGGGAGGCCAAGGTGC AGTGGAAGGTGGACAACGCCCTGCAGAGCGGCAACAGCC AGGAGAGCGTGACCGAGCAGGACAGCAAGGACAGCACC TACAGCCTGAGCAGCACCCTGACCCTGAGCAAGGCCGAC TACGAGAAGCACAAGGTGTACGCCTGCGAGGTGACCCAC CAGGGCCTGAGCAGCCCCGTGACCAAGAGCTTCAACAGG GGCGAGTGC | Nucleotide sequence of the light chain of E06 |
| 7 | DIQMTQSPATLSLSPGERATLSCRASQSVSSSYLAWYQQKP GQAPRLLIYGASSRATGIPDRFSGSGSGTDFTLTISRLEPEDF ATYYCQQSYSTPSFGQGTRLEIT | Amino acid sequence of the light chain variable domain of E06 |
| 8 | GACATCCAGATGACCCAGAGCCCCGCCACCCTGAGCCTG AGCCCCGGCGAGAGGGCCACCCTGAGCTGCAGGGCCAGC CAGAGCGTGAGCAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCACCTACTACTGCCAGCAG AGCTACAGCACCCCCAGCTTCGGCCAGGGCACCAGGCTG GAGATCACC | Nucleotide sequence of the light chain variable domain of E06 |
| 9 | WYEMY | Amino acid sequence of HCDR1 of E06 |
| 10 | SISPSGGWTMYADSVKG | Amino acid sequence of HCDR2 of E06 |
| 11 | PLYSSDGLSAGDI | Amino acid sequence of HCDR3 of E06 |
| 12 | RASQSVSSSYLA | Amino acid sequence of LCDR1 of E06 |
| 13 | GASSRAT | Amino acid sequence of LCDR2 of E06 |
| 14 | QQSYSTPS | Amino acid sequence of LCDR3 of E06 |
| 15 | SAME AS E06 | Amino acid sequence of the heavy chain of E06 germline M4 |
| 16 | SAME AS E06 | Nucleotide sequence of the heavy chain of E06 germline M4 |
| 17 | SAME AS E06 | Amino acid sequence of the heavy chain variable domain of E06 germline M4 |
| 18 | SAME AS E06 | Nucleotide sequence of the heavy chain variable domain of E06 germline M4 |
| 19 | EIVLTQSPATLSLSPGERATLSCRASQSVSSSYLAWYQQKPG QAPRLLIYGASSRATGIPDRFSGSGSGTDFTLTISRLEPEDFA VYYCQQSYSTPSFGQGTRLEITRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | Amino acid sequence of the light chain of E06 germline M4 |

-continued

| SEQ ID NO | SEQUENCE | DESCRIPTION |
|---|---|---|
| 20 | GAGATCGTGCTGACCCAGAGCCCCGCCACCCTGAGCCTG AGCCCCGGCGAGAGGGCCACCCTGAGCTGCAGGGCCAGC CAGAGCGTGAGCAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG AGCTACAGCACCCCCAGCTTCGGCCAGGGCACCAGGCTG GAGATCACCAGGACCGTGGCCGCCCCCAGCGTGTTCATC TTCCCCCCCAGCGACGAGCAGCTGAAGAGCGGCACCGCC AGCGTGGTGTGCCTGCTGAACAACTTCTACCCCAGGGAG GCCAAGGTGCAGTGGAAGGTGGACAACGCCCTGCAGAGC GGCAACAGCCAGGAGAGCGTGACCGAGCAGGACAGCAA GGACAGCACCTACAGCCTGAGCAGCACCCTGACCCTGAG CAAGGCCGACTACGAGAAGCACAAGGTGTACGCCTGCGA GGTGACCCACCAGGGCCTGAGCAGCCCCGTGACCAAGAG CTTCAACAGGGGCGAGTGC | Nucleotide sequence of the light chain of E06 germline M4 |
| 21 | EIVLTQSPATLSLSPGERATLSCRASQSVSSSYLAWYQQKPG QAPRLLIYGASSRATGIPDRFSGSGSGTDFTLTISRLEPEDFA VYYCQQSYSTPSFGQGTRLEIT | Amino acid sequence of the light chain variable domain of E06 germline M4 |
| 22 | GAGATCGTGCTGACCCAGAGCCCCGCCACCCTGAGCCTG AGCCCCGGCGAGAGGGCCACCCTGAGCTGCAGGGCCAGC CAGAGCGTGAGCAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG AGCTACAGCACCCCCAGCTTCGGCCAGGGCACCAGGCTG GAGATCACC | Nucleotide sequence of the light chain variable domain of E06 germline M4 |
| 23 | SAME AS E06 HCDR1 | Amino acid sequence of HCDR1 of E06 germline M4 |
| 24 | SAME AS E06 HCDR2 | Amino acid sequence of HCDR2 of E06 germline M4 |
| 25 | SAME AS E06 HCDR3 | Amino acid sequence of HCDR3 of E06 germline M4 |
| 26 | SAME AS E06 LCDR1 | Amino acid sequence of LCDR1 of E06 germline M4 |
| 27 | SAME AS E06 LCDR2 | Amino acid sequence of LCDR2 of E06 germline M4 |
| 28 | SAME AS E06 LCDR3 | Amino acid sequence of LCDR3 or E06 germline M4 |
| 29 | SAME AS E06 | Amino acid sequence of the heavy chain of D04 |
| 30 | SAME AS E06 | Nucleotide sequence of the heavy chain of D04 |
| 31 | SAME AS E06 | Amino acid sequence of the heavy chain variable domain of D04 |
| 32 | SAME AS E06 | Nucleotide sequence of the heavy chain variable domain of D04 |
| 33 | EIVLTQSPATLSLSPGERATLSCRASQSVHSSYLAWYQQKPG QAPRLLIYGASSRATGIPDRFSGSGSGTDFTLTISRLEPEDFA VYYCQQSYSTPSFGQGTRLEITRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | Amino acid sequence of the light chain of D04 |

-continued

| SEQ ID NO | SEQUENCE | DESCRIPTION |
|---|---|---|
| 34 | GAGATCGTGCTGACCCAGAGCCCCGCCACCCTGAGCCTG AGCCCCGGCGAGAGGGCCACCCTGAGCTGCAGGGCCAGC CAGAGCGTGCACAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG AGCTACAGCACCCCCAGCTTCGGCCAGGGCACCAGGCTG GAGATCACCAGGACCGTGGCCGCCCCCAGCGTGTTCATC TTCCCCCCCAGCGACGAGCAGCTGAAGAGCGGCACCGCC AGCGTGGTGTGCCTGCTGAACAACTTCTACCCCAGGGAG GCCAAGGTGCAGTGGAAGGTGGACAACGCCCTGCAGAGC GGCAACAGCCAGGAGAGCGTGACCGAGCAGGACAGCAA GGACAGCACCTACAGCCTGAGCAGCACCCTGACCCTGAG CAAGGCCGACTACGAGAAGCACAAGGTGTACGCCTGCGA GGTGACCCACCAGGGCCTGAGCAGCCCCGTGACCAAGAG CTTCAACAGGGGCGAGTGC | Nucleotide sequence of the light chain of D04 |
| 35 | EIVLTQSPATLSLSPGERATLSCRASQSVHSSYLAWYQQKPG QAPRLLIYGASSRATGIPDRFSGSGSGTDFTLTISRLEPEDFA VYYCQQSYSTPSFGQGTRLEIT | Amino acid sequence of the light chain variable domain of D04 |
| 36 | GAGATCGTGCTGACCCAGAGCCCCGCCACCCTGAGCCTG AGCCCCGGCGAGAGGGCCACCCTGAGCTGCAGGGCCAGC CAGAGCGTGCACAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG AGCTACAGCACCCCCAGCTTCGGCCAGGGCACCAGGCTG GAGATCACC | Nucleotide sequence of the light chain variable domain of D04 |
| 37 | SAME AS E06 HCDR1 | Amino acid sequence of HCDR1 of D04 |
| 38 | SAME AS E06 HCDR2 | Amino acid sequence of HCDR2 of D04 |
| 39 | SAME AS E06 HCDR3 | Amino acid sequence of HCDR3 of D04 |
| 40 | RASQSVHSSYLA | Amino acid sequence of LCDR1 of D04 |
| 41 | SAME AS E06 LCDR2 | Amino acid sequence of LCDR2 of D04 |
| 42 | SAME AS E06 LCDR3 | Amino acid sequence of LCDR3 of D04 |
| 43 | SAME AS E06 | Amino acid sequence of the heavy chain of J05 |
| 44 | SAME AS E06 | Nucleotide sequence of the heavy chain of J05 |
| 45 | SAME AS E06 | Amino acid sequence of the heavy chain variable domain of J05 |
| 46 | SAME AS E06 | Nucleotide sequence of the heavy chain variable domain of J05 |
| 47 | EIVLTQSPATLSLSPGERATLSCRASQSVSSSYLAWYQQKPG QAPRLLIYGASSRATGIPDRFSGSGSGTDFTLTISRLEPEDFA VYYCQQSYRTPSFGQGTRLEITRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | Amino acid sequence of the light chain of J05 |

-continued

| SEQ ID NO | SEQUENCE | DESCRIPTION |
|---|---|---|
| 48 | GAGATCGTGCTGACCCAGAGCCCCGCCACCCTGAGCCTG AGCCCCGGCGAGAGGGCCACCCTGAGCTGCAGGGCCAGC CAGAGCGTGAGCAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG AGCTACAGGACCCCCAGCTTCGGCCAGGGCACCAGGCTG GAGATCACCAGGACCGTGGCCGCCCCCAGCGTGTTCATC TTCCCCCCCAGCGACGAGCAGCTGAAGAGCGGCACCGCC AGCGTGGTGTGCCTGCTGAACAACTTCTACCCCAGGGAG GCCAAGGTGCAGTGGAAGGTGGACAACGCCCTGCAGAGC GGCAACAGCCAGGAGAGCGTGACCGAGCAGGACAGCAA GGACAGCACCTACAGCCTGAGCAGCACCCTGACCCTGAG CAAGGCCGACTACGAGAAGCACAAGGTGTACGCCTGCGA GGTGACCCACCAGGGCCTGAGCAGCCCCGTGACCAAGAG CTTCAACAGGGGCGAGTGC | Nucleotide sequence of the light chain of J05 |
| 49 | EIVLTQSPATLSLSPGERATLSCRASQSVSSSYLAWYQQKPG QAPRLLIYGASSRATGIPDRFSGSGSGTDFTLTISRLEPEDFA VYYCQQSYRTPSFGQGTRLEIT | Amino acid sequence of the light chain variable domain of J05 |
| 50 | GAGATCGTGCTGACCCAGAGCCCCGCCACCCTGAGCCTG AGCCCCGGCGAGAGGGCCACCCTGAGCTGCAGGGCCAGC CAGAGCGTGAGCAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG AGCTACAGGACCCCCAGCTTCGGCCAGGGCACCAGGCTG GAGATCACC | Nucleotide sequence of the light chain variable domain of J05 |
| 51 | SAME AS E06 HCDR1 | Amino acid sequence of HCDR1 of J05 |
| 52 | SAME AS E06 HCDR2 | Amino acid sequence of HCDR2 of J05 |
| 53 | SAME AS E06 HCDR3 | Amino acid sequence of HCDR3 of J05 |
| 54 | SAME AS E06 LCDR1 | Amino acid sequence of LCDR1 of J05 |
| 55 | SAME AS E06 LCDR2 | Amino acid sequence of LCDR2 of J05 |
| 56 | QQSYRTPS | Amino acid sequence of LCDR3 of J05 |
| 57 | SAME AS E06 | Amino acid sequence of the heavy chain of I20 |
| 58 | SAME AS E06 | Nucleotide sequence of the heavy chain of I20 |
| 59 | SAME AS E06 | Amino acid sequence of the heavy chain variable domain of I20 |
| 60 | SAME AS E06 | Nucleotide sequence of the heavy chain variable domain of I20 |
| 61 | EIVLTQSPATLSLSPGERATLSCRASQSVSSSYLAWYQQKPG QAPRLLIYGASSRATGIPDRFSGSGSGTDFTLTISRLEPEDFA VYYCQQDYSTPSFGQGTRLEITRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | Amino acid sequence of the light chain of I20 |

-continued

| SEQ ID NO | SEQUENCE | DESCRIPTION |
|---|---|---|
| 62 | GAGATCGTGCTGACCCAGAGCCCCGCCACCCTGAGCCTG AGCCCCGGCGAGAGGGCCACCCTGAGCTGCAGGGCCAGC CAGAGCGTGAGCAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG GACTACAGCACCCCCAGCTTCGGCCAGGGCACCAGGCTG GAGATCACCAGGACCGTGGCCGCCCCCAGCGTGTTCATC TTCCCCCCCAGCGACGAGCAGCTGAAGAGCGGCACCGCC AGCGTGGTGTGCCTGCTGAACAACTTCTACCCCAGGGAG GCCAAGGTGCAGTGGAAGGTGGACAACGCCCTGCAGAGC GGCAACAGCCAGGAGAGCGTGACCGAGCAGGACAGCAA GGACAGCACCTACAGCCTGAGCAGCACCCTGACCCTGAG CAAGGCCGACTACGAGAAGCACAAGGTGTACGCCTGCGA GGTGACCCACCAGGGCCTGAGCAGCCCCGTGACCAAGAG CTTCAACAGGGGCGAGTGC | Nucleotide sequence of the light chain of I20 |
| 63 | EIVLTQSPATLSLSPGERATLSCRASQSVSSSYLAWYQQKPG QAPRLLIYGASSRATGIPDRFSGSGSGTDFTLTISRLEPEDFA VYYCQQDYSTPSFGQGTRLEIT | Amino acid sequence of the light chain variable domain of I20 |
| 64 | GAGATCGTGCTGACCCAGAGCCCCGCCACCCTGAGCCTG AGCCCCGGCGAGAGGGCCACCCTGAGCTGCAGGGCCAGC CAGAGCGTGAGCAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG GACTACAGCACCCCCAGCTTCGGCCAGGGCACCAGGCTG GAGATCACC | Nucleotide sequence of the light chain variable domain of I20 |
| 65 | SAME AS E06 HCDR1 | Amino acid sequence of HCDR1 of I20 |
| 66 | SAME AS E06 HCDR2 | Amino acid sequence of HCDR2 of I20 |
| 67 | SAME AS E06 HCDR3 | Amino acid sequence of HCDR3 of I20 |
| 68 | SAME AS E06 LCDR1 | Amino acid sequence of LCDR1 of I20 |
| 69 | SAME AS E06 LCDR2 | Amino acid sequence of LCDR2 of I20 |
| 70 | QQDYSTPS | Amino acid sequence of LCDR3 of I20 |
| 71 | SAME AS E06 | Amino acid sequence of the heavy chain of H1R |
| 72 | SAME AS E06 | Nucleotide sequence of the heavy chain of H1R |
| 73 | SAME AS E06 | Amino acid sequence of the heavy chain variable domain of H1R |
| 74 | SAME AS E06 | Nucleotide sequence of the heavy chain variable domain of H1R |
| 75 | EIVLTQSPATLSLSPGERATLSCRASQSVHSSYLAWYQQKPG QAPRLLIYGASSRATGIPDRFSGSGSGTDFTLTISRLEPEDFA VYYCQQSYRTPSFGQGTRLEITRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | Amino acid sequence of the light chain of H1R |

| SEQ ID NO | SEQUENCE | DESCRIPTION |
|---|---|---|
| 76 | GAGATCGTGCTGACCCAGAGCCCCGCCACCCTGAGCCTG<br>AGCCCCGGCGAGAGGGCCACCCTGAGCTGCAGGGCCAGC<br>CAGAGCGTGCACAGCAGCTACCTGGCCTGGTACCAGCAG<br>AAGCCCGGCCAGGCCCCCAGGCTGCTGATCTACGGCGCC<br>AGCAGCAGGGCCACCGGCATCCCCGACAGGTTCAGCGGC<br>AGCGGCAGCGGCACCGACTTCACCCTGACCATCAGCAGG<br>CTGGAGCCCGAGGACTTCGCCGTGTACTACTGCCAGCAG<br>AGCTACAGGACCCCCAGCTTCGGCCAGGGCACCAGGCTG<br>GAGATCACCAGGACCGTGGCCGCCCCCAGCGTGTTCATC<br>TTCCCCCCCAGCGACGAGCAGCTGAAGAGCGGCACCGCC<br>AGCGTGGTGTGCCTGCTGAACAACTTCTACCCCAGGGAG<br>GCCAAGGTGCAGTGGAAGGTGGACAACGCCCTGCAGAGC<br>GGCAACAGCCAGGAGAGCGTGACCGAGCAGGACAGCAA<br>GGACAGCACCTACAGCCTGAGCAGCACCCTGACCCTGAG<br>CAAGGCCGACTACGAGAAGCACAAGGTGTACGCCTGCGA<br>GGTGACCCACCAGGGCCTGAGCAGCCCCGTGACCAAGAG<br>CTTCAACAGGGGCGAGTGC | Nucleotide sequence of the light chain of H1R |
| 77 | EIVLTQSPATLSLSPGERATLSCRASQSVHSSYLAWYQQKPG<br>QAPRLLIYGASSRATGIPDRFSGSGSGTDFTLTISRLEPEDFA<br>VYYCQQSYRTPSFGQGTRLEIT | Amino acid sequence of the light chain variable domain of H1R |
| 78 | GAGATCGTGCTGACCCAGAGCCCCGCCACCCTGAGCCTG<br>AGCCCCGGCGAGAGGGCCACCCTGAGCTGCAGGGCCAGC<br>CAGAGCGTGCACAGCAGCTACCTGGCCTGGTACCAGCAG<br>AAGCCCGGCCAGGCCCCCAGGCTGCTGATCTACGGCGCC<br>AGCAGCAGGGCCACCGGCATCCCCGACAGGTTCAGCGGC<br>AGCGGCAGCGGCACCGACTTCACCCTGACCATCAGCAGG<br>CTGGAGCCCGAGGACTTCGCCGTGTACTACTGCCAGCAG<br>AGCTACAGGACCCCCAGCTTCGGCCAGGGCACCAGGCTG<br>GAGATCACC | Nucleotide sequence of the light chain variable domain of H1R |
| 79 | SAME AS E06 HCDR1 | Amino acid sequence of HCDR1 of H1R |
| 80 | SAME AS E06 HCDR2 | Amino acid sequence of HCDR2 of H1R |
| 81 | SAME AS E06 HCDR3 | Amino acid sequence of HCDR3 of H1R |
| 82 | RASQSVHSSYLA | Amino acid sequence of LCDR1 of H1R |
| 83 | SAME AS E06 LCDR2 | Amino acid sequence of LCDR2 of H1R |
| 84 | QQSYRTPS | Amino acid sequence of LCDR3 of H1R |
| 85 | EVQLLESGGGLVQPGGSLRLSCAASGFTFSWYEMYWVRQA<br>PGKGLEWVSSISPSGGWTMYADSVKGRFTISRDNSKNTLYL<br>QMNSLRAEDTAVYYCATPLYSSDGLSAGDIWGQGTMVTVS<br>SASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKRVEPKSCDKTHTCPPCPAPELLGGPSVF<br>LFPPKPKDTLMISRTPEVTCVVVDVSHEDPEVKFNWYVDGV<br>EVHNAKTKPREEQYNSTYRVVSVLTVLHQDWLNGKEYKC<br>KVSNKALPAPIEKTISKAKGQPREPQVYTLPPSREEMTKNQV<br>SLTCLVKGFYPSDIAVEWESNGQPENNYKTTPPVLDSDGSFF<br>LYSKLTVDKSRWQQGNVFSCSVMHEALHNHYTQKSLSLSP<br>GK | Amino acid sequence of the heavy chain of H1RK |
| 86 | GAAGTTCAATTGTTAGAGTCTGGTGGCGGTCTTGTTCAGC<br>CTGGTGGTTCTTTACGTCTTTCTTGCGCTGCTTCCGGATTC<br>ACTTTCTCTTGGTACGAGATGTATTGGGTTCGCCAAGCTC<br>CTGGTAAAGGTTTGGAGTGGGTTTCTTCTATCTCTCCTTCT<br>GGTGGCTGGACTATGTATGCTGACTCCGTTAAAGGTCGCT<br>TCACTATCTCTAGAGACAACTCTAAGAATACTCTCTACTT<br>GCAGATGAACAGCTTAAGGGCTGAGGACACGGCCGTGTA<br>TTACTGTGCGACCCCCTTGTATAGCAGTGACGGGCTTTCG<br>GCGGGGGATATCTGGGGCCAAGGGACAATGGTCACCGTC<br>TCAAGCGCGTCGACCAAGGGCCCATCCGTCTTCCCCCTGG | Nucleotide sequence of the heavy chain of H1RK |

-continued

Sequences

| SEQ ID NO | SEQUENCE | DESCRIPTION |
|---|---|---|
| | CACCCTCCTCCAAGAGCACCTCTGGGGGCACAGCGGCCC<br>TGGGCTGCCTGGTCAAGGACTACTTCCCCGAACCGGTGA<br>CGGTGTCCTGGAACTCAGGCGCTCTGACCAGCGGCGTGC<br>ACACCTTCCCGGCTGTCCTACAGTCCTCAGGACTCTACTC<br>CCTCAGCAGCGTGGTGACCGTGCCCTCCAGCAGCTTGGG<br>CACCCAGACCTACATCTGCAACGTGAATCACAAGCCCAG<br>CAACACCAAGGTGGACAAGAGAGTTGAGCCCAAATCTTG<br>TGACAAAACTCACACATGCCCACCGTGCCCAGCACCTGA<br>ACTCCTGGGGGACCGTCAGTCTTCCTCTTCCCCCCAAAA<br>CCCAAGGACACCCTCATGATCTCCCGGACCCCTGAGGTC<br>ACATGCGTGGTGGTGGACGTGAGCCACGAAGACCCTGAG<br>GTCAAGTTCAACTGGTACGTGGACGGCGTGGAGGTGCAT<br>AATGCCAAGACAAAGCCGCGGGAGGAGCAGTACAACAG<br>CACGTACCGTGTGGTCAGCGTCCTCACCGTCCTGCACCAG<br>GACTGGCTGAATGGCAAGGAGTACAAGTGCAAGGTCTCC<br>AACAAAGCCCTCCCAGCCCCCATCGAGAAAACCATCTCC<br>AAAGCCAAAGGGCAGCCCCGAGAACCACAGGTCTACACC<br>CTGCCCCCATCCCGGGAGGAGATGACCAAGAACCAGGTC<br>AGCCTGACCTGCCTGGTCAAAGGCTTCTATCCCAGCGACA<br>TCGCCGTGGAGTGGGAGAGCAATGGGCAGCCGGAGAAC<br>AACTACAAGACCACGCCTCCCGTGCTGGACTCCGACGGC<br>TCCTTCTTCCTCTATAGCAAGCTCACCGTGGACAAGAGCA<br>GGTGGCAGCAGGGGAACGTCTTCTCATGCTCCGTGATGC<br>ATGAGGCTCTGCACAACCACTACACGCAGAAGAGCCTCT<br>CCCTGTCTCCGGGTAAA | |
| 87 | EVQLLESGGGLVQPGGSLRLSCAASGFTFSWYEMYWVRQA<br>PGKGLEWVSSISPSGGWTMYADSVKGRFTISRDNSKNTLYL<br>QMNSLRAEDTAVYYCATPLYSSDGLSAGDIWGQGTMVTVS<br>S | Amino acid sequence of the heavy chain variable domain of H1RK |
| 88 | GAAGTTCAATTGTTAGAGTCTGGTGGCGGTCTTGTTCAGC<br>CTGGTGGTTCTTTACGTCTTTCTTGCGCTGCTTCCGGATTC<br>ACTTTCTCTTGGTACGAGATGTATTGGGTTCGCCAAGCTC<br>CTGGTAAAGGTTTGGAGTGGGTTTCTTCTATCTCTCCTTCT<br>GGTGGCTGGACTATGTATGCTGACTCCGTTAAAGGTCGCT<br>TCACTATCTCTAGAGACAACTCTAAGAATACTCTCTACTT<br>GCAGATGAACAGCTTAAGGGCTGAGGACACGGCCGTGTA<br>TTACTGTGCGACCCCCTTGTATAGCAGTGACGGGCTTTCG<br>GCGGGGGATATCTGGGGCCAAGGGACAATGGTCACCGTC<br>TCAAGC | Nucleotide sequence of the heavy chain variable domain of H1RK |
| 89 | EIVLTQSPATLSLSPGERATLSCRASQSVHSSYLAWYQQKPG<br>QAPRLLIYGASSRATGIPDRFSGSGSGTDFTLTISRLEPEDFA<br>VYYCQQSYRTPSFGQGTRLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC | Amino acid sequence of the light chain of H1RK |
| 90 | GAGATCGTGCTGACCCAGTCTCCAGCCACCCTCTCTTTGT<br>CTCCAGGGGAAAGAGCCACCCTCTCCTGCAGGGCCAGTC<br>AGAGTGTTCACAGCAGCTACTTAGCCTGGTACCAGCAGA<br>AACCTGGCCAGGCTCCCAGGCTCCTCATCTATGGTGCATC<br>CAGCAGGGCCACTGGCATCCCAGACAGGTTCAGTGGCAG<br>TGGGTCTGGGACAGACTTCACTCTCACCATCAGCAGACTG<br>GAGCCTGAAGATTTTGCAGTTTACTACTGTCAACAGAGTT<br>ACCGCACCCCTTCCTTCGGCCAAGGGACACGACTGGAGA<br>TTAAACGTACGGTGGCTGCACCATCTGTCTTCATCTTCCC<br>GCCATCTGATGAGCAGTTGAAATCTGGAACTGCCTCTGTT<br>GTGTGCCTGCTGAATAACTTCTATCCCAGAGAGGCCAAA<br>GTACAGTGGAAGGTGGATAACGCCCTCCAATCGGGTAAC<br>TCCCAGGAGAGTGTCACAGAGCAGGACAGCAAGGACAG<br>CACCTACAGCCTCAGCAGCACCCTGACGCTGAGCAAAGC<br>AGACTACGAGAAACACAAAGTCTACGCCTGCGAAGTCAC<br>CCATCAGGGCCTGAGCTCGCCCGTCACAAAGAGCTTCAA<br>CAGGGGAGAGTGT | Nucleotide sequence of the light chain of H1RK |
| 91 | EIVLTQSPATLSLSPGERATLSCRASQSVHSSYLAWYQQKPG<br>QAPRLLIYGASSRATGIPDRFSGSGSGTDFTLTISRLEPEDFA<br>VYYCQQSYRTPSFGQGTRLEIK | Amino acid sequence of the light chain variable domain of H1RK |

| SEQ ID NO | SEQUENCE | DESCRIPTION |
|---|---|---|
| 92 | GAGATCGTGCTGACCCAGTCTCCAGCCACCCTCTCTTTGT CTCCAGGGGAAAGAGCCACCCTCTCCTGCAGGGCCAGTC AGAGTGTTCACAGCAGCTACTTAGCCTGGTACCAGCAGA AACCTGGCCAGGCTCCCAGGCTCCTCATCTATGGTGCATC CAGCAGGGCCACTGGCATCCCAGACAGGTTCAGTGGCAG TGGGTCTGGGACAGACTTCACTCTCACCATCAGCAGACTG GAGCCTGAAGATTTTGCAGTTTACTACTGTCAACAGAGTT ACCGCACCCCTTCCTTCGGCCAAGGGACACGACTGGAGA TTAAA | Nucleotide sequence of the light chain variable domain of H1RK |
| 93 | WYEMY | Amino acid sequence of HCDR1 of H1RK |
| 94 | SISPSGGWTMYADSVKG | Amino acid sequence of HCDR2 of H1RK |
| 95 | PLYSSDGLSAGDI | Amino acid sequence of HCDR3 of H1RK |
| 96 | RASQSVHSSYLA | Amino acid sequence of LCDR1 of H1RK |
| 97 | GASSRAT | Amino acid sequence of LCDR2 of H1RK |
| 98 | QQSYRTPS | Amino acid sequence of LCDR3 of H1RK |
| 99 | SAME AS E06 | Amino acid sequence of the heavy chain of H1DR |
| 100 | SAME AS E06 | Nucleotide sequence of the heavy chain of H1DR |
| 101 | SAME AS E06 | Amino acid sequence of the heavy chain variable domain of H1DR |
| 102 | SAME AS E06 | Nucleotide sequence of the heavy chain variable domain of H1DR |
| 103 | EIVLTQSPATLSLSPGERATLSCRASQSVHSSYLAWYQQKPG QAPRLLIYGASSRATGIPDRFSGSGSGTDFTLTISRLEPEDFA VYYCQQDYRTPSFGQGTRLEITRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | Amino acid sequence of the light chain of H1DR |
| 104 | GAGATCGTGCTGACCCAGAGCCCCGCCACCCTGAGCCTG AGCCCCGGCGAGAGGGCCACCCTGAGCTGCAGGGCCAGC CAGAGCGTGCACAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG GACTACAGGACCCCCAGCTTCGGCCAGGGCACCAGGCTG GAGATCACCAGGACCGTGGCCGCCCCCAGCGTGTTCATC TTCCCCCCCAGCGACGAGCAGCTGAAGAGCGGCACCGCC AGCGTGGTGTGCCTGCTGAACAACTTCTACCCCAGGGAG GCCAAGGTGCAGTGGAAGGTGGACAACGCCCTGCAGAGC GGCAACAGCCAGGAGAGCGTGACCGAGCAGGACAGCAA GGACAGCACCTACAGCCTGAGCAGCACCCTGACCCTGAG CAAGGCCGACTACGAGAAGCACAAGGTGTACGCCTGCGA GGTGACCCACCAGGGCCTGAGCAGCCCCGTGACCAAGAG CTTCAACAGGGGCGAGTGC | Nucleotide sequence of the light chain of H1DR |
| 105 | EIVLTQSPATLSLSPGERATLSCRASQSVHSSYLAWYQQKPG QAPRLLIYGASSRATGIPDRFSGSGSGTDFTLTISRLEPEDFA VYYCQQDYRTPSFGQGTRLEIT | Amino acid sequence of the light chain variable domain of H1DR |

-continued

Sequences

| SEQ ID NO | SEQUENCE | DESCRIPTION |
|---|---|---|
| 106 | GAGATCGTGCTGACCCAGAGCCCCGCCACCCTGAGCCTG AGCCCCGGCGAGAGGGCCACCCTGAGCTGCAGGGCCAGC CAGAGCGTGCACAGCAGCTACCTGGCCTGGTACCAGCAG AAGCCCGGCCAGGCCCCCAGGCTGCTGATCTACGGCGCC AGCAGCAGGGCCACCGGCATCCCCGACAGGTTCAGCGGC AGCGGCAGCGGCACCGACTTCACCCTGACCATCAGCAGG CTGGAGCCCGAGGACTTCGCCGTGTACTACTGCCAGCAG GACTACAGGACCCCCAGCTTCGGCCAGGGCACCAGGCTG GAGATCACC | Nucleotide sequence of the light chain variable domain of H1DR |
| 107 | SAME AS E06 HCDR1 | Amino acid sequence of HCDR1 of H1DR |
| 108 | SAME AS E06 HCDR2 | Amino acid sequence of HCDR2 of H1DR |
| 109 | SAME AS E06 HCDR3 | Amino acid sequence of HCDR3 of H1DR |
| 110 | RASQSVHSSYLA | Amino acid sequence of LCDR1 of H1DR |
| 111 | SAME AS E06 LCDR2 | Amino acid sequence of LCDR2 of H1DR |
| 112 | QQDYRTPS | Amino acid sequence of LCDR3 of H1DR |

EXAMPLES

For the experiments described herein various antibodies were used including, Avastin® (Ferrara, N et al. Biochem Biophys Res Comm, 333:328-335, 2005), G6-31 (Liang, W C et al. J Biol Chem, 281: 951-961, 2006), B20-4.1 (Liang, W C et al. J Biol Chem, 281: 951-961, 2006), and an isotype control, designated R347, as a monospecific or a bispecific antibody as needed. An anti-VEGF IgG1 antibody capable of binding all VEGF isoforms that is not cross-reactive with mouse can used as a positive control for some binding and functional studies. Where cross reactivity to mouse VEGF is needed the antibodies G6-31 and B20-4.1 can be used as a positive control.

Example 1: Identification of Anti-VEGF Antibodies from Phage Antibody Display Libraries Solution phage panning was applied to isolate anti-VEGF antibodies from antibody phage libraries. The phage libraries were incubated with biotinylated VEGF165 (PeproTech, N.J.) at the final concentration of 4 μg/ml (human VEGF165 for first and third round and mVEGF164 for the second and fourth round panning). After incubation for 30 minutes, the VEGF bound phages were captured from the solution by adding straptavidin beads (Invitrogen), which were pre-washed with phosphate buffer saline (PBS) and blocked with 3% bovine serum albumin (BSA) in PBS. The beads captured phages were eluted with 100 mM TEA buffer, neutralized with 1 M Tris-HCI (pH8.0), and then 1 ml of eluted phage were used to infect 5 ml of log phase TG1 and 4 ml of 2YT medium (Teknova) for phage amplification. After incubation at 37° C. for 30 minutes in water bath, the cells were spun down at 4000 g, resuspended in 2YT, spread on 2YT agar plates (Teknova) with 100 μg/ml of carbenicillin and 2% glucose, and incubated at 30° C. overnight. On the second day, the colonies were collected from the agar plates, inoculated into 2YT medium at the final density of OD600=0.1, grown at 37° C. until log phase, infected with helper phage (Invitrogen) and then let it grow overnight in 2YT with carbenicillin (Invitrogen) and kanamycin (Sigma) at 30° C. to generate high titer phages. The amplified phages were precipitated with PEG8000, resuspended in PBS and used for the next round of panning using the standard procedure. A total of four rounds of panning were applied to isolate VEGF specific antibodies. A significant enrichment of output phage numbers was observed from $2 \times 10^5$ pfu in the first round to $4 \times 10^7$ pfu in the fourth round of panning.

Example 2: Screening of VEGF Specific Antibodies

Specificity of individual phage Fab from the fourth round of panning was assessed by phage ELISA. The 96-well microtiter plates were coated with human VEGF165 at a concentration of 5 μg/ml in PBS at 40° C. overnight. After being washed three times with PBS, the wells were blocked with the blocking buffer (4% skimmed milk in PBS) for 1 h at 37° C. Then, 50 μl/well phage was added and incubated for 1 h at 37° C. After washing, 50 μl of horseradish peroxidase (HRP)-conjugated mouse anti-M13 (Amersham Pharmacia) in blocking buffer with 1:1,000 dilution was added for 30 minutes at 37° C. For detection, 50 μl/well of SureBlue Reserve TMB substrate (KPL) for 5 minutes at room temperature and the reaction was stopped by adding 50 μL of TMB Stop Solution (KPL). The absorbance was read at 450 nm. After four rounds of panning, more than 50% of clones are VEGF specific with absorbance higher than 1, which is 20-fold higher than the nonspecific background reading approximately 0.05. Representative data is show in Table 1.

TABLE 1

| 1 | 2 | 3 | 4 | 5 | 6 | 7 | 8 | 9 | 10 | 11 | 12 |
|---|---|---|---|---|---|---|---|---|---|---|---|
| 0.091 | 2.276 | 2.406 | 0.111 | 0.116 | 0.116 | 0.087 | 2.534 | 0.059 | 2.478 | 0.098 | 0.193 |
| 0.091 | 2.755 | 3.161 | 1.508 | 0.054 | 3.166 | 0.062 | 0.066 | 0.061 | 3.2 | 2.354 | 1.971 |
| 2.328 | 0.078 | 2.697 | 2.919 | 3.216 | 3.258 | 3.133 | 2.948 | 2.859 | 2.6 | 1.314 | 2.595 |
| 2.209 | 3.056 | 0.084 | 3.139 | 3.181 | 0.055 | 3.336 | 2.472 | 3.074 | 0.062 | 2.741 | 0.073 |
| 0.05 | 0.052 | 0.053 | 3.02 | 3.57 | 0.049 | 0.047 | 2.862 | 2.761 | 2.609 | 0.051 | 0.05 |
| 0.05 | 0.05 | 0.053 | 2.861 | 3.469 | 3.155 | 0.057 | 0.387 | 1.325 | 0.052 | 3.067 | 2.446 |
| 1.963 | 2.641 | 3.27 | 3.349 | 3.246 | 0.047 | 3.509 | 2.727 | 0.046 | 2.67 | 2.679 | 0.053 |
| 0.044 | 0.05 | 3.105 | 0.053 | 3.215 | 2.483 | 0.059 | 3.004 | 2.294 | 2.994 | 3.091 | 1.336 |

Example 3-Binding of Clone E06 to Human and Mouse VEGF

After initial phage screening, one clone (E06) with cross-reactivity to mouse VEGF164 was further converted and expressed as the full length IgG using standard molecular biology materials and methods. The 96-well microtiter plates (Corning) were coated with 50 μl/well of human and mouse VEGF165 or VEGF121 at a concentration of 5 μg/ml in PBS at 4° C. overnight. After being washed three times with PBS containing 0.1% Tween-20 (PBST), the wells were blocked with blocking buffer (4% skimmed milk in PBS). After 1 h incubation at room temperature, the plates were washed with PBST and a 2-fold serial dilution of the antibodies (starting from 8 nM) in blocking buffer were added and incubated for 1 hour at room temperature. The antibody solution was removed by washing with PBST followed by 1 hour incubation at room temperature with a 1:3000 dilution of an anti-human-Fc-HRP antibody (Thermo Scientific) prepared in PBST. Binding was visualized with the addition of 50 μL of SureBlue Reserve TMB substrate (KPL) for 5 minutes at room temperature and the reaction was stopped by adding 50 μL of TMB Stop Solution (KPL). The absorbance at 450 nm was measured using a microtiter plate reader. The data were analyzed using Prism 5 software (GraphPad).

Similar binding activity of antibody E06 to human VEGF165 and mouse VEGF164 was observed with an EC50 of 0.048 nM and 0.049 nM, respectively. As expected, Avastin® (an anti-VEGF antibody) showed strong binding to human VEGF165 but no detectable binding to mouse VEGF164. The isotype control antibody R347 did not bind either human or mouse forms of VEGF. Representative data are shown in FIG. 1.

Figure 2:
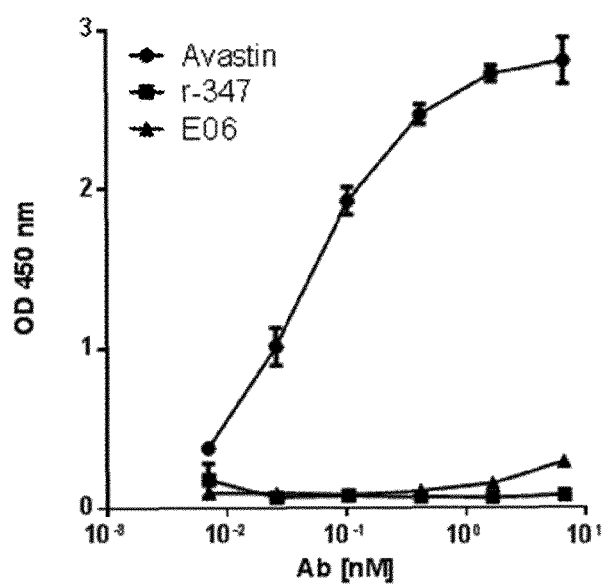
FIG. 2. Representative data demonstrating lack of binding to VEGF121.

To evaluate whether antibody E06 binds to a different epitope than Avastin® (an anti-VEGF antibody), an ELISA assay was conducted using human VEGF121. Avastin® (an anti-VEGF antibody) showed very strong binding to human VEGF121. However, no binding was deteceted for E06, indicating antibody E06 binds to a different epitope than Avastin® (an anti-VEGF antibody). The isotype control antibody R347 also did not demonstrate any binding to human VEGF121. Representative data are shown in FIG. 2.

Example 4-Germline of Clone E06

Framework sequences of clone E06 were engineered to match to its closest germline sequences. A sequence analysis against the IgG germline gene database showed that the E06 VL sequence best matches to the germline gene VK3-NL5*01 with 4 amino acid differences at positions 1, 3, 4 and 86 of the VL. Although the VH sequence is identical to the germline gene VH3-23*2, the T98 differs from most conserved germline amino acid of R or K at this position. To germline E06, four variants were designed and expressed. These variants substitute partially or totally with the germline gene encoded amino acids at the positions that E06 sequence differs from the best matched germline genes. For instance, M1 contains D1E/Q3V/M4L substitutions in the VL and T98R substitution in the VH; M4 contains D1E/Q3V/M4L/T86V substitutions in the VL; M7 contains D1E/Q3V/M4L/T86V substitutions in the VL and T98R substitution in the VH; and F1 contains the D1E/Q3V/M4L substitutions in the VL, where the first letter represents the one letter amino acid code of the original and the second letter represents the one letter amino acid code of the germline sequence. FIG. 3 shows the sequence alignment of the parental E06 and the most homologous germline genes.

The germline variants were expressed and purified as Fabs and their binding to the recombinant VEGF165 was determined by ELISA. The binding results showed that the germline variants M4 and F1, which contain the full or partial VL germline amino acid substitutions retained E06 WT Fab binding activity. In addition, M4 showed similar activity compared to the WT E06 Fab in pVEGFR2 assay using HUVECs. On the other hand, germline variants M1 and M7 containing the VH germline amino acid substitution at position T98 demonstrated drastically reduced binding and pVEGFR2 phosphorylation, indicating that T98 participated in binding and activity and must be retained. The germline clone, M4, was used as the template for further affinity optimization.

Example 5-Affinity Optimization

Each amino acid of all 6 CDRs of germline clone M4 was individually mutated to the other 20 amino acids using a hybridization mutagenesis method (Kunkel, Proc. Natl. Acad. Sci. USA Vol. 82, pp. 488-492, 1985). Two sets of DNA primers, one containing a NSS codon encoding 8 amino acids and the other containing a NWS codon encoding 12 different amino acids, were used to introduce mutations to each targeted CDR position. The individual degenerate primers were used in hybridization mutagenesis reactions. Briefly, each degenerate primer was phosphorylated and used in a 10:1 ratio with the uridinylated M4 Fab ssDNA. The mixture was heated to 95° C. then cooled down to 55° C. over 1 hour. Thereafter, T4 ligase and T7 DNA polymerase were added and the mix was incubated for 1.5 hours at 37° C. Synthesis products for VH and VL CDRs were pooled respectively; however, NSS and NWS libraries were kept separate and screened independently. Typically, 1 μL of the pooled library DNA was electroporated into XL1-Blue for plaque formation on XL1-Blue bacterial lawn or for production of Fab fragments (Wu H, An LL. Tailoring kinetics of antibodies using focused combinatorial libraries. Methods Mol Biol 2003; 207:213-33). These mutants were then screened for activity.

The primary screen consisted of a single point ELISA (SPE) assay which was carried out using culture supernatant of bacteria grown in 96-well plates (deep well) and infected with individual recombinant M13 clones as described elsewhere (Wu H, An LL. Tailoring kinetics of antibodies using focused combinatorial libraries. Methods Mol Biol 2003; 207:213-33). Briefly, this capture ELISA involved coating individual wells of a 96-well Maxisorp Immunoplate with approximately 50 ng of a sheep anti-human Fd antibody (Biodesign International, ME) in a carbonate buffer at pH 8.5 overnight at 4° C. The next day, the plate was blocked with 3% BSA in PBS buffer for 1 hour at room temperature. Fab supernatant was then added to the plate and incubated at room temperature for 1 hour. After washing, the biotinylated VEGF165 protein was added to the well and the mixture was incubated for 1.5 hours at room temperature. This was followed by incubation with neutravidin-horseradish peroxidase (HRP) conjugate (Pierce, Ill.) for approximately 40 minutes at room temperature. HRP activity was detected with tetra-methyl-benzidine (TMB) substrate and the reaction quenched with 0.2 M H2SO4. Plates were read at 450 nm.

Clones exhibiting an optical density (OD) signal at 450 nm greater than the parental clone M4 Fab were picked and regrown (15 mL) (Wu H, An LL. Tailoring kinetics of antibodies using focused combinatorial libraries. Methods Mol Biol 2003; 207:213-33) and re-assayed by ELISA (as described above) in duplicate to confirm positive results. Clones that repeatedly exhibited a signal greater than that of the M4 Fab were sequenced. The Fab protein concentration of each clone that had a CDR change was then determined by a quantitative Fab ELISA, where a Fab with known concentration was used as a reference. The Fab concentration was determined by comparing the ELISA signals with the signals generated by the reference Fab. The binding assay was repeated once more for all positive variants under normalized Fab concentrations in order to determine the relative binding affinity of the mutant Fabs and the parental M4 Fab.

Figure 4:
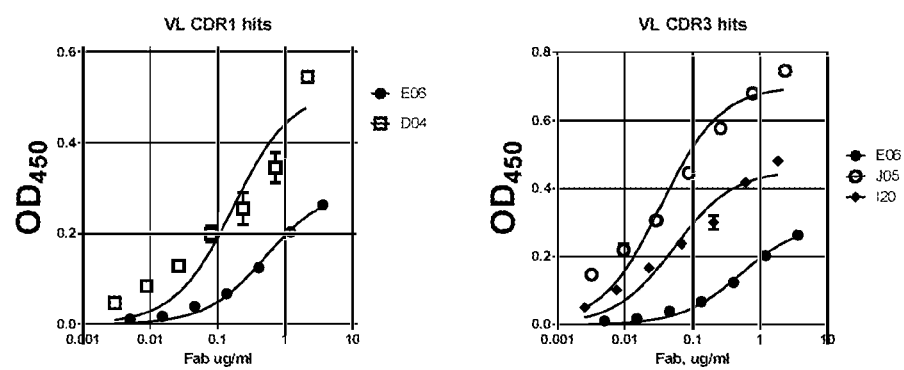
FIG. 4. Representative data demonstrating improved binding of affinity optimized variants.

Many point mutations showed binding improvements over M4 to VEGF165. Among those mutants, D04, J05, and I20 showed in excess of 10-fold improvement in EC50 compared to germline E06 as Fabs. Representative data are shown in FIG. 4. Sequence analysis revealed that amino acid substitutions that benefit to the VEGF165 binding are found in the VL, especially in the VL-CDR3. For example, a point mutation S94R in mutant J05 improved binding approximately 25-fold over E06, indicating key contributions of this amino acid in binding.

Figure 5:
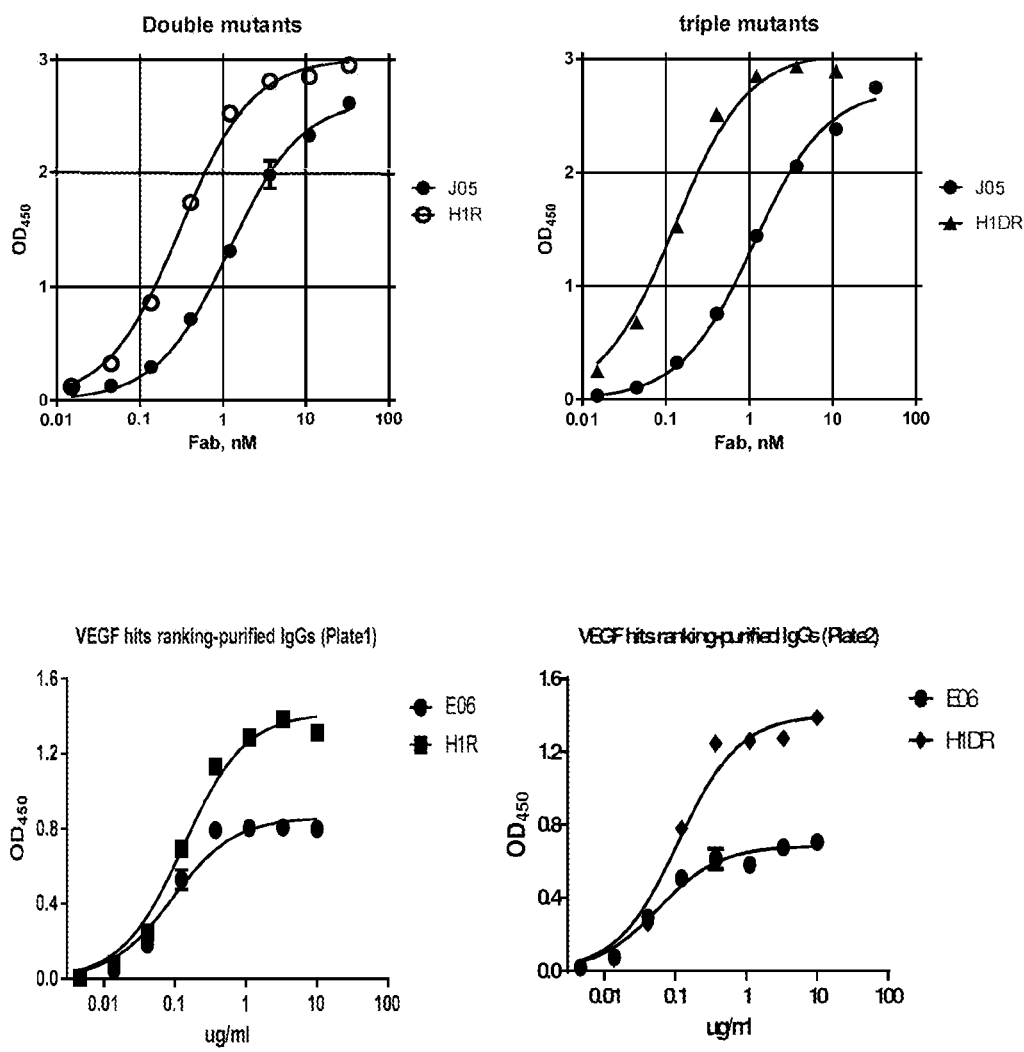
FIG. 5. Representative data demonstrating improved binding of affinity optimized variants as Fabs and IgGs. Fabs are shown in the top two graphs. IgGs are shown in the bottom two graphs.

The point mutants demonstrating improved binding were then combined using site-directed mutagenesis methods. The combination mutants were expressed as Fabs and IgGs and tested in a VEGF165 ELISA. Representative data are shown in FIG. 5.

Combination mutants showed significantly higher binding than a point mutant, J05, in an ELISA assay. The apparent binding affinity of the combination mutants was improved approximately 3- to 10-fold over J05 as Fabs. Similarly, all combination mutants tested as IgGs showed significant binding improvement compared to the parental clone E06. The equilibrium binding constants (KD) of the affinity optimized clones were measurements using KinExA. Representative data are shown in Table 2. Sequences of point mutants as well as combination mutants are shown in Table 3.

TABLE 2

| IgG | $K_D$, pM (95% CI) (Std. Aff. model - ref [VEGF165]) | FoldΔ $K_D$ vs. E06-wt |
|---|---|---|
| H1R | 23.2 (10.8-40.9) | 109 |
| J05 | 220.3 (179.1-268.4) | 11 |
| Wt (E06) | 2520 (1800-4260) | — |
| Avastin ® | 99.9 (71.1-137.0) | 25 |

TABLE 3

(The CDR 1 column discloses SEQ ID NOS 113-114, 113, 113-114, and 114, respectively, in order of appearance, and the CDR 3 column discloses 115, 115-117, 116, and 118, respectively, in order of appearance)

| VL | CDR1 | CDR3 |
|---|---|---|
| E06 | R A S Q S V S S S Y L A | Q Q S Y S T P S |
| D04 | R A S Q S V H S S Y L A | Q Q S Y S T P S |
| J05 | R A S Q S V S S S Y L A | Q Q S Y R T P S |
| I20 | R A S Q S V S S S Y L A | Q Q D Y S T P S |
| H1R | R A S Q S V H S S Y L A | Q Q S Y R T P S |
| H1DR | R A S Q S V H S S Y L A | Q Q D Y R T P S |

Example 6-Measurement of Kd for the Binding of Avastin, E06 and Affinity Optimized E06 Variants to Human VEGF165

Equilibrium binding constant (KD) measurements were performed on KinExA 3000 and 3200 instruments (Sapidyne Instruments, Boise, Id.). Human VEGF165 (huVEGF) protein was coated onto UltraLink® Biosupport beads (PIERCE, Rockford, Ill.) at concentrations of 2 ug/mL, 3 ug/mL, and 30 ug/mL in coating buffer (50 mM sodium carbonate buffer, pH 9). Coated beads were then separated (spin) from unreacted huVEGF protein solution, and blocked with 1M Tris, pH 8, containing BSA at 10 mg/mL), for approximately 15 minutes at room temperature. After this, the bead slurry was spun to remove the blocking solution, and then the block step was repeated for approximately 2 hours using fresh block buffer, and stored at 4° C. until used. Prior to use, the huVEGF-coated beads were transferred to a bead vial, resuspended in approximately 27 mLs of instrument buffer (10 mM HEPES+300 mM NaCl+5 mM $CaCl_2$+0.05% P20+0.02% $NaN_3$, pH8), and affixed to the KinExA instrument. For the KD measurements, separate solutions of antibodies were prepared at 100 pM and 2.5 nM concentrations in instrument buffer containing BSA (mg/mL), then dispensed into two separate series of 13 tubes. These concentrations of mAbs were chosen to allow each KD measurement to be made under both receptor- and KD-controlled conditions, leading to more rigorous estimations of reagent activity and affinity, respectively. Owing to its relatively weak KD, a 3rd concentration series (50 nM) for mAb E06-wt was also prepared to satisfy the requirement for a fully receptor-controlled measurement. Two-fold serial dilutions of huVEGF protein were then titrated across 9 of the tubes in each mAb series, followed by two additional 10-fold-dilutions, leaving one tube as the mAb-only, "zero" control. In so doing, this yielded concentration series' of huVEGF protein that ranged from 488 fM-25 nM (100 pM mAb experiments), 3.91 pM-200 nM (2.5 nM mAb experiments), and 9.77 pM-500 nM (50 nM mAb experiment). Based on theory curve simulations available through the vendor software (Sapidyne Instruments, Boise, Idaho), the mixtures were incubated 1-4 days at room temperature to allow binding to reach equilibrium. At the end of this time, signal-testing experiments were conducted to determine the appropriate run conditions for each set of measurements. Detection of free antibody was made possible using a species-specific, secondary antibody reagent (Goat Anti-Human IgG (H+L)-DyLight649, Part #109-495-088, Jackson ImmunoResearch Laboratories), employed at 0.75 ug/mL, 1.0 ug/mL or 2 ug/mL in instrument buffer containing BSA at 1 mg/mL. Data obtained for each mAb/huVEGF interaction was then simultaneously fit to a one-site binding model using the vendor's software to obtain the equilibrium KDs. The KD of the affinity optimized clones were measured using KinExA and with results summarized in Table 2.

Example 7- Assaying Affinity Optimized Variants for Binding to Murine VEGF164

Figure 6:
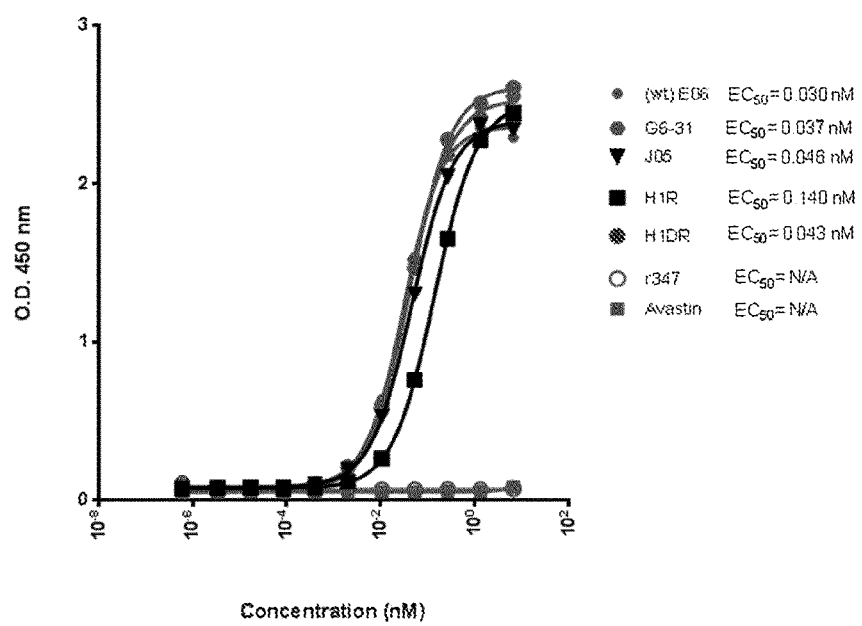
FIG. 6. Representative data demonstrating binding of affinity optimized variants to murine VEGF164.

Affinity optimized variants were screened to confirm binding to murine VEGF164, similarly as previously described for VEGF165 ELISA except with murine VEGF164. EC50 values were determined using non-linear regression analysis (log dose response, 4-parameter fit curves) in GraphPad Prism, version 5.01 (San Diego, Calif.). Representative data are shown in FIG. 6. All affinity optimized variants exhibited strong binding to murine VEGF164, similar to the parental E06 antibody.

Example 8- Assaying Affinity Optimized Variants for Reduced Binding to VEGF121

Figure 7:
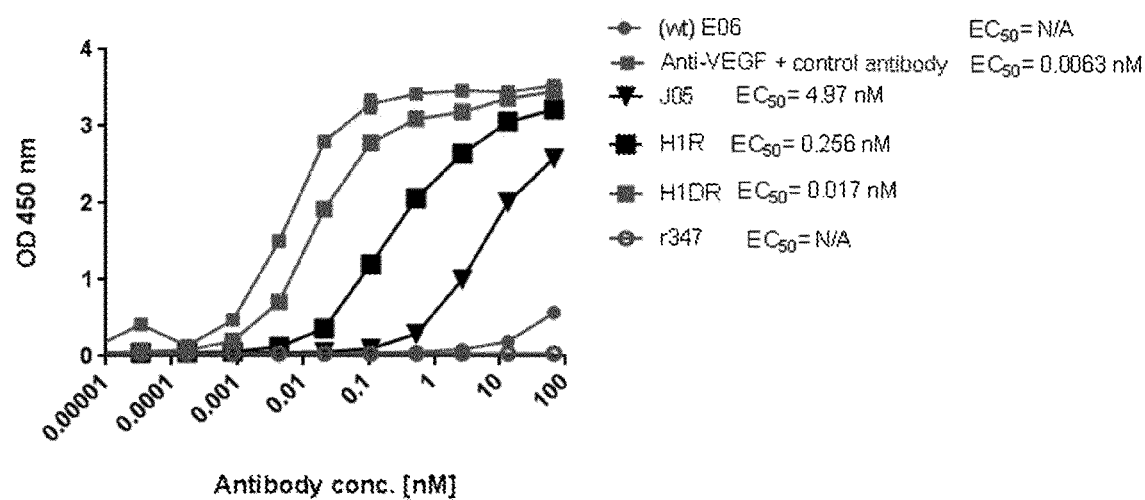
FIG. 7. Representative data demonstrating lack of binding of affinity optimized variants to VEGF121.

Affinity optimized variants were screened to confirm reduced binding to human VEGF121 in an ELISA, similarly as previously described for VEGF165 ELISA. EC50 values were determined using non-linear regression analysis (log dose response, 4-parameter fit curves) in GraphPad Prism, version 5.01 (San Diego, Calif.). Representative data are shown in FIG. 7. VEGF121 binding was reduced for J05, H1R, and H1DR in contrast to the VEGF positive control antibody with strong binding to VEGF121 (EC50 of 0.0063 nM).

Example 9- Assaying Affinity Optimized Variants for Binding to VEGF189

Affinity optimized variant screening for binding to VEGF189 is in an ELISA format. 96-well half well maxisorp plates will be coated with 25 µl of 2 µg/mL human VEGF189 (R&D Systems), diluted in PBS without Ca++ or Mg++, and refrigerated overnight. Plates will be decanted, then blocked for 1.5 hours at 37° C. with 180 µl of Blocking Buffer containing 3% BSA (Sigma, Cat #A-3059) and 0.1% Tween-20 in 1×PBS. Plates will be washed 3 times with 1×PBS containing 0.1% Tween-20. 50 µl of 6.7 nM and serial dilutions of affinity optimized variants, a positive control, and a negative control in blocking buffer is added in duplicate and incubated at 37° C. for 1 hour. Plates will be washed 3 times with wash buffer, then 50 µl of 1:5000 goat anti-human HRP IgG H+L (Jackson Immunoresearch) is added to each well and incubated at room temperature for 1 hour. Plates will developed by adding 50 µl of TMB solution (KPL) to each well, followed by stopping the reaction with 50 µl of 1M phosphoric acid. Plates will be read at 450 nm using a microplate reader. Affinity optimized variants show a decrease in binding to VEGF189.

Figure 8:
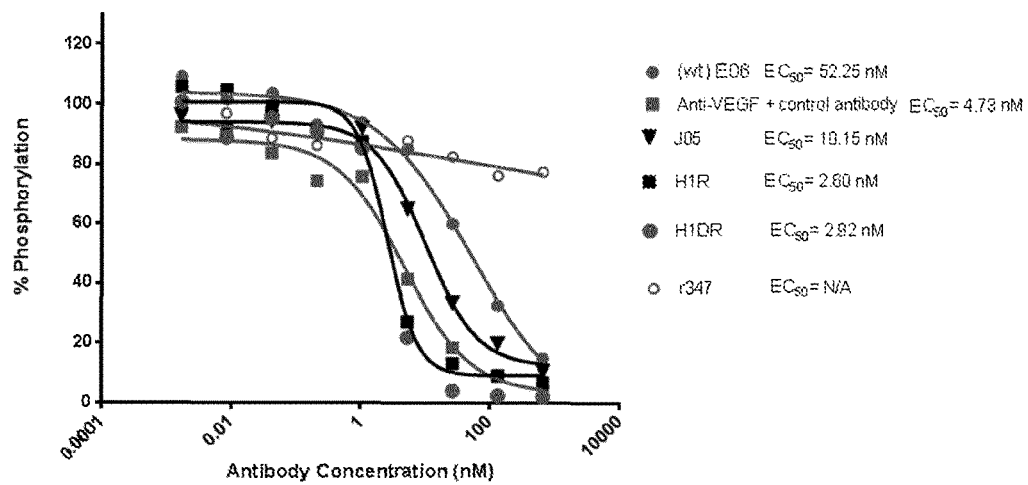
FIG. 8 A-B. Representative data demonstrating activity of affinity optimized variants in functional cell-based assays.
Figure 8:
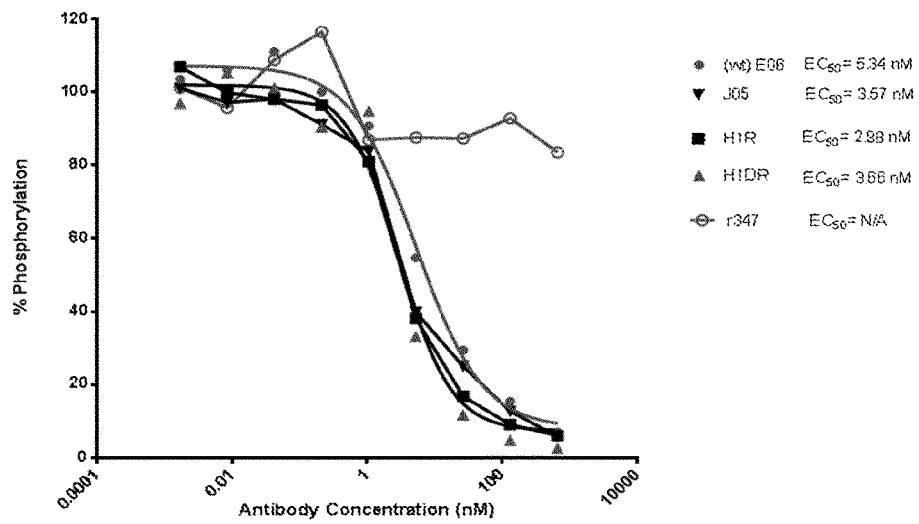

Example 10- Functional Cell-Based Assays to Compare Potency of Affinity Optimized Variants Human and murine pVEGFR2 cell based assays were performed as previously described to confirm potency of affinity optimized variants. EC50 values were determined using non-linear regression analysis (log dose response, 4-parameter fit curves) in GraphPad Prism, version 5.01 (San Diego, Calif.). Representative data are shown in FIGS. 8A and 8B. Clones J05, H1R, and H1DR exhibited up to 20-fold improvement (EC50 range 2.6-10.15 nM) vs. the E06 parental control (EC50=52.25 nM) in the human pVEGFR2 assay (FIG. 8A), while improvement in the mouse pVEGFR2 assay was up to 2-fold compared to the parental antibody (EC50 range 2.38-3.57 nM vs 5.34 nM (FIG. 8B)).

Example 11- In Vivo Activity of Affinity Optimized E06 Variants

Affinity optimized variant testing for in vivo activity will be carried out in a retinal vasculogenesis model, and a 786-0 renal cell carcinoma and B×PC3 pancreatic carcinoma model. In addition to these models, evaluation in a thrombocytopenia model will be carried out.

Figure 9:
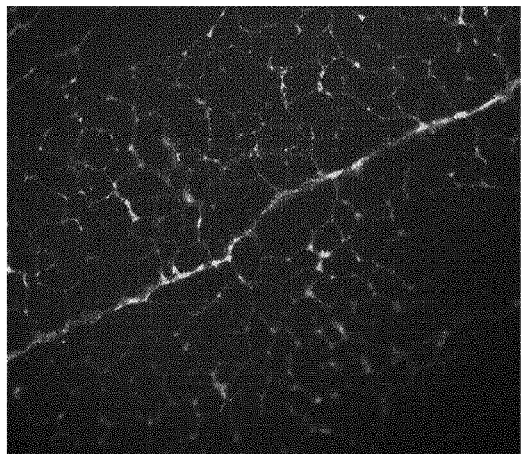
FIG. 9. Representative data demonstrating activity of an affinity optimized variant in a retinal vasculogenesis model.
Figure 9:
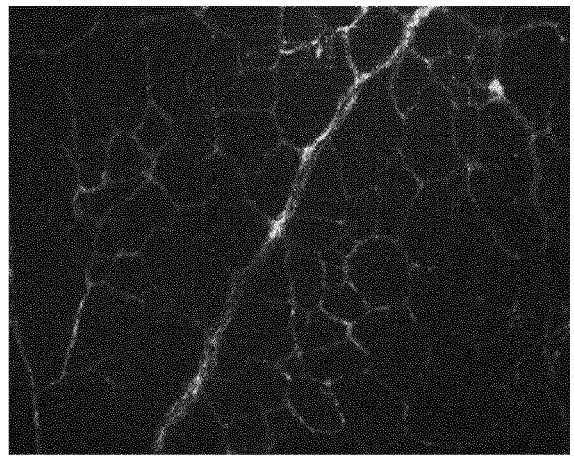

For the retinal vasculogenesis model, CD1 mice were intraperitoneally dosed at birth, days 1, 3, and 5. At day 8 the mice were anesthetized and were infused with fluorescein-labeled dextran. Eyes were removed and fixed with 10% formalin before preparation of flat mounts. Flat mounts were examined by fluorescence microscopy. Neonatal retinal angiogenesis is comprised of two processes, namely, vessel migration from the optic nerve to the edge of the retina and branching. There is a decrease in branching in the presence of H1RK compared to the untreated group. Representative data are shown in FIG. 9. H1RK differs from H1R in that the light chain at position 107 (germline corrected position at 107) contains a threonine instead of a lysine.

For the 786-0 renal cell carcinoma model, 786-0 fragments will be implanted subcutaneously into the right flank. After tumor volume reaches approximately 200 mm³, mice will be put on treatment. Mice will be treated 2× per week for a total of 6 doses. The affinity optimized variants demonstrate effectiveness at reducing tumor growth, reducing tumor volume, or reducing tumor growth and tumor volume. In addition to reducing tumor growth, reducing tumor volume, or reducing tumor growth and tumor volume, the affinity optimized variants also reduce tumor vasculature. Briefly, mice will be pretreated with heparin to prevent blood clotting 15 minutes prior to euthanasia. A solution of 0.1 mM sodium nitroprusside will be perfused at a rate of approximately 6 mL/min. Microfil MV-122 will be prepared by mixing 8 mL of lates, 10 mL of diluent and 900 uL of cure. After the mixture settles (1 minute) it will be perfused at a rate of approximately 2 mL/min until a total volume of 17 mL is administered. After 60-90 minutes the tumor will be dissected and immersed in 10% NBF for 24 hours. The sample will then be transferred to 25% ETOH/PBS, 50% ETOH/PBS, 75% ETOH/PBS, 95% ETOH, and then 100% ETOH for 24 hours each. After the final incubation the sample will be immersed in methyl salicylate to clear the dehydrated tumor sample before imaging by light microscopy.

For the BxPC3 pancreatic carcinoma model, female SCID mice will be implanted subcutaneously into the right flank. After tumor volume reaches approximately 200 mm³, mice will be put on treatment. Mice will be treated 2× per week for a total of 6 doses. The affinity optimized variants demonstrate effectiveness at reducing tumor growth, reducing tumor volume, or reducing tumor growth and tumor volume. In addition to reducing tumor growth, reducing tumor volume, or reducing tumor growth and tumor volume, the affinity optimized variants also reduce tumor vasculature.

For the thrombocytopenia model, a method will be used that is adopted from Meyer et al, 2009 (J Thromb Haemost 7:171-81, 2009). Briefly FC gamma receptor 2A transgenic mice, 8-16 weeks old will be injected with premixed VEGF$_{165}$, 0.6 units heparin, and an affinity optimized variant into the lateral tail vein. Mice will then be observed for behavioral signs of distress and scored as: (−) stopped and moved constantly from corner to corner, breathing normal, (+) signs of lethargy, stopped and moved in longer duration, breathing shallow, (++) very lethargic, stopped moving, staying in mostly one side of the box, breathing deeply, (+++) sever thrombotic event-twitching and twirling, (++++) death. The affinity optimized variants demonstrate a reduction in thrombocytopenia as compared to the anti-VEGF control.

Incorporation by Reference

All references cited herein, including patents, patent applications, papers, text books, and the like, and the references cited therein, to the extent that they are not already, are hereby incorporated herein by reference in their entireties for all purposes.

Equivalents

The foregoing written specification is considered to be sufficient to enable one skilled in the art to practice the embodiments. It will be appreciated, however, that no matter how detailed the foregoing may appear in text, the embodiments may be practiced in many ways and the claims include any equivalents thereof.

What is claimed is:

1. An isolated nucleic acid molecule comprising polynucleotides encoding an antibody comprising heavy chain complementarity determining regions 1-3 (HCDR1, HCDR2, and HCDR3) and light chain complementarity determining regions 1-3 (LCDR1, LCDR2, and LCDR3), wherein HCDR1, HCDR2, and HCDR3 and LCDR1, LCDR2, and LCDR3 comprise SEQ ID NOs: 79-84, respectively.

2. A vector comprising the nucleic acid molecule of claim 1.

3. A cell comprising the vector of claim 2.

4. A method of making an antibody comprising culturing a cell comprising the vector of claim 2.

* * * * *

SEQUENCE LISTING

```
<160> NUMBER OF SEQ ID NOS: 122

<210> SEQ ID NO 1
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 2
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaggtgcagc tgctggagag cggcggcggc ctggtgcagc ccggcggcag cctgaggctg      60
agctgcgccg ccagcggctt caccttcagc tggtacgaga tgtactgggt gaggcaggcc     120
cccggcaagg gcctggagtg ggtgagcagc atcagcccca gcggcggctg gaccatgtac     180
gccgacagcg tgaagggcag gttcaccatc agcagggaca cagcaagaa cacccctgtac     240 ctgcagatga acagcctgag ggccgaggac accgccgtgt actactgcgc cacccccctg     300
tacagcagcg acggcctgag cgccggcgac atctggggcc agggcaccat ggtgaccgtg     360
agcagcgcca gcaccaaggg ccccagcgtg ttccccctgg cccccagcag caagagcacc     420
agcggcggca ccgccgccct gggctgcctg gtgaaggact acttccccga gcccgtgacc     480
gtgagctgga acagcggcgc cctgaccagc ggcgtgcaca ccttccccgc cgtgctgcag     540
agcagcggcc tgtacagcct gagcagcgtg gtgaccgtgc ccagcagcag cctgggcacc     600

```
cagacctaca tctgcaacgt gaaccacaag cccagcaaca ccaaggtgga caagagggtg    660
gagcccaaga gctgcgacaa gacccacacc tgccccccct gccccgcccc cgagctgctg    720
ggcggcccca gcgtgttcct gttccccccc aagcccaagg acaccctgat gatcagcagg    780 accccgagg tgacctgcgt ggtggtggac gtgagccacg aggaccccga ggtgaagttc      840
aactggtacg tggacggcgt ggaggtgcac aacgccaaga ccaagcccag ggaggagcag    900
tacaacagca cctacagggt ggtgagcgtg ctgaccgtgc tgcaccagga ctggctgaac    960
ggcaaggagt acaagtgcaa ggtgagcaac aaggccctgc ccgcccccat cgagaagacc    1020
atcagcaagg ccaagggcca gccccaggag ccccaggtgt acaccctgcc ccccagcagg    1080
gaggagatga ccaagaacca ggtgagcctg acctgcctgg tgaagggctt ctaccccagc    1140
gacatcgccg tggagtggga gagcaacggc cagcccgaga caactacaa gaccaccccc     1200 cccgtgctgg acagcgacgg cagcttcttc ctgtacagca agctgaccgt ggacaagagc    1260
aggtggcagc agggcaacgt gttcagctgc agcgtgatgc acgaggccct gcacaaccac    1320
tacacccaga gagcctgag cctgagcccc ggcaag                               1356
```

<210> SEQ ID NO 3
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
        115                 120
```

<210> SEQ ID NO 4
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
gaggtgcagc tgctggagag cggcggcggc ctggtgcagc ccggcggcag cctgaggctg    60
agctgcgccg ccagcggctt caccttcagc tggtacgaga tgtactgggt gaggcaggcc    120
cccggcaagg gcctggagtg ggtgagcagc atcagcccca gcggcggctg gaccatgtac    180
gccgacagcg tgaagggcag gttcaccatc agcagggaca acagcaagaa caccctgtac    240
```

```
ctgcagatga acagcctgag ggccgaggac accgccgtgt actactgcgc caccccctg      300 tacagcagcg acggcctgag cgccggcgac atctggggcc agggcaccat ggtgaccgtg      360
agcagc                                                                 366
```

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys Gln Gln Ser Tyr Ser Thr Pro
                85                  90                  95

Ser Phe Gly Gln Gly Thr Arg Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 6
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
gacatccaga tgacccagag ccccgccacc ctgagcctga gccccggcga gagggccacc      60
ctgagctgca gggccagcca gagcgtgagc agcagctacc tggcctggta ccagcagaag      120
cccggccagg cccccaggct gctgatctac ggcgccagca gcagggccac cggcatcccc      180
gacaggttca gcggcagcgg cagcggcacc gacttcaccc tgaccatcag caggctggag      240
```

```
cccgaggact tcgccaccta ctactgccag cagagctaca gcaccccag cttcggccag      300 ggcaccaggc tggagatcac caggaccgtg ccgcccca gcgtgttcat cttccccccc       360
agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga aagcacaag gtgtacgcct gcgaggtgac ccaccagggc      600
ctgagcagcc ccgtgaccaa gagcttcaac agggcgagt gc                         642
```

```
<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys Gln Gln Ser Tyr Ser Thr Pro
                85                  90                  95

Ser Phe Gly Gln Gly Thr Arg Leu Glu Ile Thr
            100                 105
```

```
<210> SEQ ID NO 8
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gacatccaga tgacccagag ccccgccacc ctgagcctga gccccggcga gagggccacc      60
ctgagctgca gggccagcca gagcgtgagc agcagctacc tggcctggta ccagcagaag    120
cccggccagg cccccaggct gctgatctac ggcgccagca gcagggccac cggcatcccc    180
gacaggttca gcggcagcgg cagcggcacc gacttcaccc tgaccatcag caggctggag    240
cccgaggact tcgccaccta ctactgccag cagagctaca gcaccccag cttcggccag     300 ggcaccaggc tggagatcac c                                              321
```

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Trp Tyr Glu Met Tyr
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Ile Ser Pro Ser Gly Gly Trp Thr Met Tyr Ala Asp Ser Val Lys
1               5                   10                  15

Gly

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Leu Tyr Ser Ser Asp Gly Leu Ser Ala Gly Asp Ile
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Gln Ser Val Ser Ser Ser Tyr Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ala Ser Ser Arg Ala Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Ser Tyr Ser Thr Pro Ser
1               5

<210> SEQ ID NO 15
<211> LENGTH: 452
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 16
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gaggtgcagc tgctggagag cggcggcggc ctggtgcagc ccggcggcag cctgaggctg    60
agctgcgccg ccagcggctt caccttcagc tggtacgaga tgtactgggt gaggcaggcc   120
cccggcaagg gcctggagtg ggtgagcagc atcagcccca gcggcggctg gaccatgtac   180
gccgacagcg tgaagggcag gttcaccatc agcagggaca cagcaagaa caccctgtac   240 ctgcagatga acagcctgag ggccgaggac accgccgtgt actactgcgc caccccctg   300 tacagcagcg acggcctgag cgccggcgac atctggggcc agggcaccat ggtgaccgtg   360
agcagcgcca gcaccaaggg ccccagcgtg ttccccctgg cccccagcag caagagcacc   420
agcggcggca ccgccgccct gggctgcctg gtgaaggact acttccccga gcccgtgacc   480
gtgagctgga acagcggcgc cctgaccagc ggcgtgcaca ccttcccgc cgtgctgcag   540 agcagcggcc tgtacagcct gagcagcgtg gtgaccgtgc ccagcagcag cctgggcacc   600
cagacctaca tctgcaacgt gaaccacaag cccagcaaca ccaaggtgga caagagggtg   660
gagcccaaga gctgcgacaa gacccacacc tgcccccct gccccgcccc cgagctgctg   720
ggcggcccca gcgtgttcct gttcccccc aagcccaagg acaccctgat gatcagcagg   780
acccccgagg tgacctgcgt ggtggtggac gtgagccacg aggaccccga ggtgaagttc   840
aactggtacg tggacggcgt ggaggtgcac aacgccaaga ccaagcccag ggaggagcag   900
tacaacagca cctacagggt ggtgagcgtg ctgaccgtgc tgcaccagga ctggctgaac   960
ggcaaggagt acaagtgcaa ggtgagcaac aaggccctgc cgcccccat cgagaagacc  1020 atcagcaagg ccaagggcca gcccagggag cccagggtgt acaccctgcc cccagcagg  1080 gaggagatga ccaagaacca ggtgagcctg acctgctgg tgaagggctt ctaccccagc  1140
gacatcgccg tggagtggga gagcaacggc cagcccgaga caactacaa gaccaccccc  1200 cccgtgctgg acagcgacgg cagcttcttc ctgtacagca agctgaccgt ggacaagagc  1260
aggtggcagc agggcaacgt gttcagctgc agcgtgatgc acgaggccct gcacaaccac  1320
tacacccaga gagcctgag cctgagcccc ggcaag                             1356

<210> SEQ ID NO 17
<211> LENGTH: 122
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
        115                 120
```

<210> SEQ ID NO 18
<211> LENGTH: 366
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18

```
gaggtgcagc tgctggagag cggcggcggc ctggtgcagc ccggcggcag cctgaggctg    60
agctgcgccg ccagcggctt caccttcagc tggtacgaga tgtactgggt gaggcaggcc   120
cccggcaagg gcctggagtg ggtgagcagc atcagcccca gcggcggctg gaccatgtac   180
gccgacagcg tgaagggcag gttcaccatc agcagggaca acagcaagaa caccctgtac   240
ctgcagatga acagcctgag ggccgaggac accgccgtgt actactgcgc cacccccctg   300
tacagcagcg acggcctgag cgccggcgac atctgggggcc agggcaccat ggtgaccgtg   360
agcagc                                                              366
```

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 19

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Ser Tyr Ser Thr Pro
                85                  90                  95

Ser Phe Gly Gln Gly Thr Arg Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gagatcgtgc tgacccagag ccccgccacc ctgagcctga gccccggcga gagggccacc      60
ctgagctgca gggccagcca gagcgtgagc agcagctacc tggcctggta ccagcagaag     120
cccggccagg cccccaggct gctgatctac ggcgccagca gcagggccac cggcatcccc     180
gacaggttca gcggcagcgg cagcggcacc gacttcaccc tgaccatcag caggctggag     240
cccgaggact cgccgtgta ctactgccag cagagctaca gcacccccag cttcggccag     300
ggcaccaggc tggagatcac caggaccgtg gccgccccca gcgtgttcat cttcccccc      360 agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga gaagcacaag gtgtacgcct gcgaggtgac ccaccagggc     600
ctgagcagcc ccgtgaccaa gagcttcaac agggcgagt gc                         642

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu

```
                35                  40                  45
Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ser Tyr Ser Thr Pro
                 85                  90                  95

Ser Phe Gly Gln Gly Thr Arg Leu Glu Ile Thr
            100                 105

<210> SEQ ID NO 22
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gagatcgtgc tgacccagag ccccgccacc ctgagcctga gccccggcga gagggccacc      60
ctgagctgca gggccagcca gagcgtgagc agcagctacc tggcctggta ccagcagaag     120
cccggccagg cccccaggct gctgatctac ggcgccagca gcagggccac cggcatcccc     180
gacaggttca gcggcagcgg cagcggcacc gacttcaccc tgaccatcag caggctggag     240
cccgaggact tcgccgtgta ctactgccag cagagctaca gcacccccag cttcggccag     300
ggcaccaggc tggagatcac c                                               321

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Tyr Glu Met Tyr
1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ile Ser Pro Ser Gly Gly Trp Thr Met Tyr Ala Asp Ser Val Lys
1               5                   10                  15

Gly

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Leu Tyr Ser Ser Asp Gly Leu Ser Ala Gly Asp Ile
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ala Ser Gln Ser Val Ser Ser Ser Tyr Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ala Ser Ser Arg Ala Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gln Ser Tyr Ser Thr Pro Ser
1               5

<210> SEQ ID NO 29
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

| | | | | | | | | | | | |
|---|---|---|---|---|---|---|---|---|---|---|---|
|Ser|Val|Phe|Pro|Leu|Ala|Pro|Ser|Ser|Lys|Ser|Thr Ser Gly Gly Thr|
| |130| | | |135| | | |140| | |
|Ala|Ala|Leu|Gly|Cys|Leu|Val|Lys|Asp|Tyr|Phe|Pro Glu Pro Val Thr|
|145| | | | |150| | | |155| | 160|
|Val|Ser|Trp|Asn|Ser|Gly|Ala|Leu|Thr|Ser|Gly|Val His Thr Phe Pro|
| | | |165| | | | |170| | | 175|
|Ala|Val|Leu|Gln|Ser|Ser|Gly|Leu|Tyr|Ser|Leu|Ser Ser Val Val Thr|
| | | |180| | | | |185| | |190|
|Val|Pro|Ser|Ser|Ser|Leu|Gly|Thr|Gln|Thr|Tyr|Ile Cys Asn Val Asn|
| | |195| | | | |200| | | |205|
|His|Lys|Pro|Ser|Asn|Thr|Lys|Val|Asp|Lys|Arg|Val Glu Pro Lys Ser|
| |210| | | | |215| | | |220| |
|Cys|Asp|Lys|Thr|His|Thr|Cys|Pro|Pro|Cys|Pro|Ala Pro Glu Leu Leu|
|225| | | |230| | | | |235| | 240|
|Gly|Gly|Pro|Ser|Val|Phe|Leu|Phe|Pro|Pro|Lys|Pro Lys Asp Thr Leu|
| | | | |245| | | |250| | | 255|
|Met|Ile|Ser|Arg|Thr|Pro|Glu|Val|Thr|Cys|Val|Val Val Asp Val Ser|
| | | |260| | | | |265| | | 270|
|His|Glu|Asp|Pro|Glu|Val|Lys|Phe|Asn|Trp|Tyr|Val Asp Gly Val Glu|
| | |275| | | | |280| | | |285|
|Val|His|Asn|Ala|Lys|Thr|Lys|Pro|Arg|Glu|Glu|Gln Tyr Asn Ser Thr|
| |290| | | | |295| | | |300| |
|Tyr|Arg|Val|Val|Ser|Val|Leu|Thr|Val|Leu|His|Gln Asp Trp Leu Asn|
|305| | | | |310| | | |315| | 320|
|Gly|Lys|Glu|Tyr|Lys|Cys|Lys|Val|Ser|Asn|Lys|Ala Leu Pro Ala Pro|
| | | |325| | | | |330| | | 335|
|Ile|Glu|Lys|Thr|Ile|Ser|Lys|Ala|Lys|Gly|Gln|Pro Arg Glu Pro Gln|
| | | |340| | | | |345| | | 350|
|Val|Tyr|Thr|Leu|Pro|Pro|Ser|Arg|Glu|Glu|Met|Thr Lys Asn Gln Val|
| | |355| | | | |360| | | |365|
|Ser|Leu|Thr|Cys|Leu|Val|Lys|Gly|Phe|Tyr|Pro|Ser Asp Ile Ala Val|
| |370| | | | |375| | | |380| |
|Glu|Trp|Glu|Ser|Asn|Gly|Gln|Pro|Glu|Asn|Asn|Tyr Lys Thr Thr Pro|
|385| | | | |390| | | |395| | 400|
|Pro|Val|Leu|Asp|Ser|Asp|Gly|Ser|Phe|Phe|Leu|Tyr Ser Lys Leu Thr|
| | | |405| | | | |410| | | 415|
|Val|Asp|Lys|Ser|Arg|Trp|Gln|Gln|Gly|Asn|Val|Phe Ser Cys Ser Val|
| | | |420| | | | |425| | | 430|
|Met|His|Glu|Ala|Leu|His|Asn|His|Tyr|Thr|Gln|Lys Ser Leu Ser Leu|
| | | |435| | | | |440| | | 445|
|Ser|Pro|Gly|Lys| | | | | | | | |
| |450| | | | | | | | | | |

```
<210> SEQ ID NO 30
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gaggtgcagc tgctggagag cggcggcggc ctggtgcagc ccggcggcag cctgaggctg      60
agctgcgccg ccagcggctt caccttcagc tggtacgaga tgtactgggt gaggcaggcc     120
cccggcaagg gcctggagtg ggtgagcagc atcagcccca gcggcggctg gaccatgtac     180
```

```
gccgacagcg tgaagggcag gttcaccatc agcagggaca acagcaagaa cacccctgtac    240 ctgcagatga acagcctgag ggccgaggac accgccgtgt actactgcgc cacccccctg    300
tacagcagcg acggcctgag cgccggcgac atctggggcc agggcaccat ggtgaccgtg    360
agcagcgcca gcaccaaggg ccccagcgtg ttccccctgg cccccagcag caagagcacc    420
agcggcggca ccgccgccct gggctgcctg gtgaaggact acttccccga gccgtgacc     480 gtgagctgga acagcggcgc cctgaccagc ggcgtgcaca ccttcccgc cgtgctgcag     540 agcagcggcc tgtacagcct gagcagcgtg gtgaccgtgc ccagcagcag cctgggcacc    600
cagacctaca tctgcaacgt gaaccacaag cccagcaaca ccaaggtgga caagagggtg    660
gagcccaaga gctgcgacaa gacccacacc tgcccccct gccccgcccc cgagctgctg    720
ggcggcccca gcgtgttcct gttccccccc aagcccaagg acacctgat gatcagcagg    780 acccccgagg tgacctgcgt ggtggtggac gtgagccacg aggaccccga ggtgaagttc    840
aactggtacg tggacggcgt ggaggtgcac aacgccaaga ccaagcccag ggaggagcag    900
tacaacagca cctacagggt ggtgagcgtg ctgaccgtgc tgcaccagga ctggctgaac    960
ggcaaggagt acaagtgcaa ggtgagcaac aaggccctgc cgccccat cgagaagacc     1020 atcagcaagg ccaagggcca gccagggag ccccaggtgt acaccctgcc ccccagcagg    1080
gaggagatga ccaagaacca ggtgagcctg acctgcctgg tgaagggctt ctaccccagc    1140
gacatcgccg tggagtggga gagcaacggc cagcccgaga caactacaa gaccaccccc    1200 cccgtgctgg acagcgacgg cagcttcttc ctgtacagca agctgaccgt ggacaagagc    1260
aggtggcagc agggcaacgt gttcagctgc agcgtgatgc acgaggccct gcacaaccac    1320
tacacccaga agagcctgag cctgagcccc ggcaag                              1356
```

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
        115                 120
```

<210> SEQ ID NO 32
<211> LENGTH: 366

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 32
gaggtgcagc tgctggagag cggcggcggc ctggtgcagc ccggcggcag cctgaggctg     60
agctgcgccg ccagcggctt caccttcagc tggtacgaga tgtactgggt gaggcaggcc    120
cccggcaagg gcctggagtg ggtgagcagc atcagcccca gcggcggctg gaccatgtac    180
gccgacagcg tgaagggcag gttcaccatc agcagggaca acagcaagaa cacccctgta    240
ctgcagatga acagcctgag ggccgaggac accgccgtgt actactgcgc cacccccctg    300
tacagcagcg acggcctgag cgccggcgac atctggggcc agggcaccat ggtgaccgtg    360
agcagc                                                                366

<210> SEQ ID NO 33
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Ser Thr Pro
                85                  90                  95

Ser Phe Gly Gln Gly Thr Arg Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 642
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 34

```
gagatcgtgc tgacccagag ccccgccacc ctgagcctga gccccggcga gagggccacc    60
ctgagctgca gggccagcca gagcgtgcac agcagctacc tggcctggta ccagcagaag   120
cccggccagg cccccaggct gctgatctac ggcgccagca gagggccac cggcatcccc    180
gacaggttca gcggcagcgg cagcggcacc gacttcaccc tgaccatcag caggctggag   240
cccgaggact cgccgtgta ctactgccag cagagctaca gccccccag cttcggccag    300
ggcaccaggc tggagatcac caggaccgtg gccgccccca gcgtgttcat cttccccccc   360
agcgacgagc agctgaagag cggcaccgcc agcgtggtgt gcctgctgaa caacttctac   420
cccagggagg ccaaggtgca gtggaaggtg acaacgccc tgcagagcgg caacagccag   480
gagagcgtga ccgagcagga cagcaaggac agcacctaca gcctgagcag caccctgacc   540
ctgagcaagg ccgactacga aagcacaag gtgtacgcct gcgaggtgac ccaccagggc   600
ctgagcagcc ccgtgaccaa gagcttcaac aggggcgagt gc                     642
```

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Ser Thr Pro
                85                  90                  95

Ser Phe Gly Gln Gly Thr Arg Leu Glu Ile Thr
            100                 105
```

<210> SEQ ID NO 36
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gagatcgtgc tgacccagag ccccgccacc ctgagcctga gccccggcga gagggccacc    60
ctgagctgca gggccagcca gagcgtgcac agcagctacc tggcctggta ccagcagaag   120
cccggccagg cccccaggct gctgatctac ggcgccagca gagggccac cggcatcccc    180
gacaggttca gcggcagcgg cagcggcacc gacttcaccc tgaccatcag caggctggag   240
```

```
cccgaggact tcgccgtgta ctactgccag cagagctaca gcaccccag cttcggccag    300 ggcaccaggc tggagatcac c                                              321
```

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Tyr Glu Met Tyr
1               5

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ile Ser Pro Ser Gly Gly Trp Thr Met Tyr Ala Asp Ser Val Lys
1               5                   10                  15
Gly

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Leu Tyr Ser Ser Asp Gly Leu Ser Ala Gly Asp Ile
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ala Ser Gln Ser Val His Ser Ser Tyr Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ala Ser Ser Arg Ala Thr
1               5

<210> SEQ ID NO 42

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Ser Tyr Ser Thr Pro Ser
1               5

<210> SEQ ID NO 43
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 44
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gaggtgcagc tgctggagag cggcggcggc ctggtgcagc ccggcggcag cctgaggctg      60
agctgcgccg ccagcggctt caccttcagc tggtacgaga tgtactgggt gaggcaggcc     120
cccggcaagg gcctggagtg ggtgagcagc atcagcccca gcggcggctg gaccatgtac     180
gccgacagcg tgaagggcag gttcaccatc agcagggaca cagcaagaa caccctgtac     240 ctgcagatga acagcctgag ggccgaggac accgccgtgt actactgcgc cacccccctg     300
tacagcagcg acgccctgag cgccggcgac atctggggcc agggcaccat ggtgaccgtg     360
agcagcgcca gcaccaaggg ccccagcgtg ttccccctgg cccccagcag caagagcacc     420
agcggcggca ccgccgccct gggctgcctg gtgaaggact acttccccga gcccgtgacc     480
gtgagctgga acagcggcgc cctgaccagc ggcgtgcaca ccttccccgc cgtgctgcag     540
agcagcggcc tgtacagcct gagcagcgtg gtgaccgtgc ccagcagcag cctgggcacc     600
cagacctaca tctgcaacgt gaaccacaag cccagcaaca ccaaggtgga caagagggtg     660
gagcccaaga gctgcgacaa gacccacacc tgccccccct gccccgcccc cgagctgctg     720
ggcggcccca gcgtgttcct gttccccccc aagcccaagg acaccctgat gatcagcagg     780
acccccgagg tgacctgcgt ggtggtggac gtgagccacg aggaccccga ggtgaagttc     840
aactggtacg tggacggcgt ggaggtgcac aacgccaaga ccaagcccag ggaggagcag     900
tacaacagca cctacagggt ggtgagcgtg ctgaccgtgc tgcaccagga ctggctgaac     960
ggcaaggagt acaagtgcaa ggtgagcaac aaggccctgc cgccccccat cgagaagacc    1020
atcagcaagg ccaagggcca gcccagggag ccccaggtgt acaccctgcc ccccagcagg    1080
gaggagatga ccaagaacca ggtgagcctg acctgcctgg tgaagggctt ctaccccagc    1140

```
gacatcgccg tggagtggga gagcaacggc cagcccgaga caactacaa gaccaccccc    1200 cccgtgctgg acagcgacgg cagcttcttc ctgtacagca agctgaccgt ggacaagagc    1260
aggtggcagc agggcaacgt gttcagctgc agcgtgatgc acgaggccct gcacaaccac    1320
tacacccaga gagcctgag cctgagcccc ggcaag                               1356
```

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
        115                 120
```

<210> SEQ ID NO 46
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
gaggtgcagc tgctggagag cggcggcggc ctggtgcagc ccggcggcag cctgaggctg    60
agctgcgccg ccagcggctt caccttcagc tggtacgaga tgtactgggt gaggcaggcc    120
cccggcaagg gcctggagtg ggtgagcagc atcagcccca gcggcggctg gaccatgtac    180
gccgacagcg tgaagggcag gttcaccatc agcagggaca acagcaagaa caccctgtac    240
ctgcagatga acagcctgag ggccgaggac accgccgtgt actactgcgc caccccccctg    300 tacagcagcg acggcctgag cgccggcgac atctggggcc agggcaccat ggtgaccgtg    360
agcagc                                                               366
```

<210> SEQ ID NO 47
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro
                85                  90                  95

Ser Phe Gly Gln Gly Thr Arg Leu Glu Ile Thr Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 48
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gagatcgtgc tgacccagag ccccgccacc ctgagcctga gccccggcga gagggccacc    60
ctgagctgca gggccagcca gagcgtgagc agcagctacc tggcctggta ccagcagaag   120
cccggccagg cccccaggct gctgatctac ggcgccagca gagggccac cggcatcccc   180
gacaggttca gcggcagcgg cagcggcacc gacttcaccc tgaccatcag caggctggag   240
cccgaggact tcgccgtgta ctactgccag cagagctaca ggacccccag cttcggccag   300
ggcaccaggc tggagatcac caggaccgtg gccgccccca gcgtgttcat cttcccccc    360
agcgacgagc agctgaagag cggcaccgcc agcgtggtgt gcctgctgaa caacttctac   420
cccagggagg ccaaggtgca gtggaaggtg gacaacgccc tgcagagcgg caacagccag   480
gagagcgtga ccgagcagga cagcaaggac agcacctaca gcctgagcag cacccctgacc   540
ctgagcaagg ccgactacga gaagcacaag gtgtacgcct gcgaggtgac ccaccagggc   600
ctgagcagcc ccgtgaccaa gagcttcaac aggggcgagt gc                      642

<210> SEQ ID NO 49
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro
                85                  90                  95

Ser Phe Gly Gln Gly Thr Arg Leu Glu Ile Thr
            100                 105

<210> SEQ ID NO 50
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gagatcgtgc tgacccagag ccccgccacc ctgagcctga gccccggcga gagggccacc        60
ctgagctgca gggccagcca gagcgtgagc agcagctacc tggcctggta ccagcagaag       120
cccggccagg cccccaggct gctgatctac ggcgccagca gcagggccac cggcatcccc       180
gacaggttca gcggcagcgg cagcggcacc gacttcaccc tgaccatcag caggctggag       240
cccgaggact tcgccgtgta ctactgccag cagagctaca ggacccccag cttcggccag       300
ggcaccaggc tggagatcac c                                                 321

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Tyr Glu Met Tyr
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Ile Ser Pro Ser Gly Gly Trp Thr Met Tyr Ala Asp Ser Val Lys
1               5                   10                  15
```

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Leu Tyr Ser Ser Asp Gly Leu Ser Ala Gly Asp Ile
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Ser Val Ser Ser Ser Tyr Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ala Ser Ser Arg Ala Thr
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Ser Tyr Arg Thr Pro Ser
1               5

<210> SEQ ID NO 57
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

```
Ser Ser Ile Ser Pro Ser Gly Gly Trp Thr Met Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Thr Pro Leu Tyr Ser Ser Asp Gly Leu Ser Ala Gly Asp Ile Trp
            100                 105                 110
Gly Gln Gly Thr Met Val Thr Val Ser Ser Ala Ser Thr Lys Gly Pro
            115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Arg Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly Lys
450
```

<210> SEQ ID NO 58
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
gaggtgcagc tgctggagag cggcggcggc ctggtgcagc ccggcggcag cctgaggctg      60
agctgcgccg ccagcggctt caccttcagc tggtacgaga tgtactgggt gaggcaggcc     120
cccggcaagg gcctggagtg ggtgagcagc atcagcccca gcggcggctg gaccatgtac     180
gccgacagcg tgaagggcag gttcaccatc agcagggaca cagcaagaa caccctgtac     240
ctgcagatga acagcctgag ggccgaggac accgccgtgt actactgcgc cacccccctg     300
tacagcagcg acggcctgag cgccggcgac atctggggcc agggcaccat ggtgaccgtg     360
agcagcgcca gcaccaaggg ccccagcgtg ttccccctgg cccccagcag caagagcacc     420
agcggcggca ccgccgccct gggctgcctg gtgaaggact acttccccga gcccgtgacc     480
gtgagctgga acagcggcgc cctgaccagc ggcgtgcaca ccttccccgc cgtgctgcag     540
agcagcggcc tgtacagcct gagcagcgtg gtgaccgtgc ccagcagcag cctgggcacc     600
cagacctaca tctgcaacgt gaaccacaag cccagcaaca ccaaggtgga caagagggtg     660
gagcccaaga gctgcgacaa gacccacacc tgcccccccct gccccgcccc cgagctgctg     720
ggcggcccca gcgtgttcct gttcccccccc aagcccaagg acaccctgat gatcagcagg     780
accccccgagg tgacctgcgt ggtggtggac gtgagccacg aggaccccga ggtgaagttc     840
aactggtacg tggacggcgt ggaggtgcac aacgccaaga ccaagcccag ggaggagcag     900
tacaacagca cctacagggt ggtgagcgtg ctgaccgtgc tgcaccagga ctggctgaac     960
ggcaaggagt acaagtgcaa ggtgagcaac aaggccctgc ccgcccccat cgagaagacc    1020
atcagcaagg ccaagggcca gccccaggag ccccaggtgt acaccctgcc ccccagcagg    1080
gaggagatga ccaagaacca ggtgagcctg acctgcctgg tgaagggctt ctaccccagc    1140
gacatcgccg tggagtggga gagcaacggc cagcccgaga caactacaa gaccacccccc    1200
cccgtgctgg acagcgacgg cagcttcttc ctgtacagca agctgaccgt ggacaagagc    1260
aggtggcagc agggcaacgt gttcagctgc agcgtgatgc acgaggccct gcacaaccac    1320
tacacccaga agagcctgag cctgagcccc ggcaag                              1356
```

<210> SEQ ID NO 59
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
            115                 120
```

```
<210> SEQ ID NO 60
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gaggtgcagc tgctggagag cggcggcggc ctggtgcagc ccggcggcag cctgaggctg        60
agctgcgccg ccagcggctt caccttcagc tggtacgaga tgtactgggt gaggcaggcc       120
cccggcaagg gcctggagtg ggtgagcagc atcagcccca gcggcggctg gaccatgtac       180
gccgacagcg tgaagggcag gttcaccatc agcagggaca cagcaagaa caccctgtac        240 ctgcagatga acagcctgag ggccgaggac accgccgtgt actactgcgc cacccccctg       300
tacagcagcg acggcctgag cgccggcgac atctggggcc agggcaccat ggtgaccgtg       360
agcagc                                                                 366
```

```
<210> SEQ ID NO 61
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Tyr Ser Thr Pro
                 85                  90                  95

Ser Phe Gly Gln Gly Thr Arg Leu Glu Ile Thr Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
gagatcgtgc tgacccagag ccccgccacc ctgagcctga gccccggcga gagggccacc    60
ctgagctgca gggccagcca gagcgtgagc agcagctacc tggcctggta ccagcagaag   120
cccggccagg cccccaggct gctgatctac ggcgccagca gcagggccac cggcatcccc   180
gacaggttca gcggcagcgg cagcggcacc gacttcaccc tgaccatcag caggctggag   240
cccgaggact tcgccgtgta ctactgccag caggactaca gcacccccag cttcggccag   300
ggcaccaggc tggagatcac caggaccgtg gccgccccca gcgtgttcat cttcccccc    360 agcgacgagc agctgaagag cggcaccgcc agcgtggtgt gcctgctgaa caacttctac   420
cccagggagg ccaaggtgca gtggaaggtg gacaacgccc tgcagagcgg caacagccag   480
gagagcgtga ccgagcagga cagcaaggac agcacctaca gcctgagcag caccctgacc   540
ctgagcaagg ccgactacga gaagcacaag gtgtacgcct gcgaggtgac ccaccagggc   600
ctgagcagcc ccgtgaccaa gagcttcaac aggggcgagt gc                     642

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Ser Thr Pro
                85                  90                  95

Ser Phe Gly Gln Gly Thr Arg Leu Glu Ile Thr
            100                 105

<210> SEQ ID NO 64
<211> LENGTH: 321

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gagatcgtgc tgacccagag ccccgccacc ctgagcctga gccccggcga gagggccacc    60
ctgagctgca gggccagcca gagcgtgagc agcagctacc tggcctggta ccagcagaag   120
cccggccagg cccccaggct gctgatctac ggcgccagca gcagggccac cggcatcccc   180
gacaggttca gcggcagcgg cagcggcacc gacttcaccc tgaccatcag caggctggag   240
cccgaggact cgccgtgta ctactgccag caggactaca gcaccccag cttcggccag     300 ggcaccaggc tggagatcac c                                              321

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Trp Tyr Glu Met Tyr
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Ile Ser Pro Ser Gly Gly Trp Thr Met Tyr Ala Asp Ser Val Lys
1               5                   10                  15

Gly

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Leu Tyr Ser Ser Asp Gly Leu Ser Ala Gly Asp Ile
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ala Ser Gln Ser Val Ser Ser Ser Tyr Leu Ala
1               5                   10
```

-continued

```
<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Ala Ser Ser Arg Ala Thr
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Asp Tyr Ser Thr Pro Ser
1               5

<210> SEQ ID NO 71
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220
```

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 72
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gaggtgcagc tgctggagag cggcggcggc ctggtgcagc ccggcggcag cctgaggctg      60
agctgcgccg ccagcggctt caccttcagc tggtacgaga tgtactgggt gaggcaggcc     120
cccggcaagg gcctggagtg ggtgagcagc atcagcccca gcggcggctg gaccatgtac     180
gccgacagcg tgaagggcag gttcaccatc agcagggaca cagcaagaa caccctgtac     240 ctgcagatga acagcctgag ggccgaggac accgccgtgt actactgcgc cccccctg      300 tacagcagcg acggcctgag cgccggcgac atctggggcc agggcaccat ggtgaccgtg     360
agcagcgcca gcaccaaggg ccccagcgtg ttccccctgg cccccagcag caagagcacc     420
agcggcggca ccgccgccct gggctgcctg gtgaaggact acttccccga gcccgtgacc     480
gtgagctgga acagcggcgc cctgaccagc ggcgtgcaca ccttccccgc cgtgctgcag     540
agcagcggcc tgtacagcct gagcagcgtg gtgaccgtgc ccagcagcag cctgggcacc     600
cagacctaca tctgcaacgt gaaccacaag cccagcaaca ccaaggtgga caagagggtg     660

```
gagcccaaga gctgcgacaa gacccacacc tgccccccct gccccgcccc cgagctgctg    720
ggcggcccca gcgtgttcct gttccccccc aagcccaagg acaccctgat gatcagcagg    780
acccccgagg tgacctgcgt ggtggtggac gtgagccacg aggaccccga ggtgaagttc    840
aactggtacg tggacggcgt ggaggtgcac aacgccaaga ccaagcccag ggaggagcag    900
tacaacagca cctacagggt ggtgagcgtg ctgaccgtgc tgcaccagga ctggctgaac    960
ggcaaggagt acaagtgcaa ggtgagcaac aaggccctgc cgcccccat cgagaagacc    1020 atcagcaagg ccaagggcca gccccagggag ccccaggtgt acaccctgcc cccagcagg    1080 gaggagatga ccaagaacca ggtgagcctg acctgcctgg tgaagggctt ctaccccagc    1140
gacatcgccg tggagtggga gagcaacggc cagcccgaga caactacaa gaccaccccc    1200 cccgtgctgg acagcgacgg cagcttcttc ctgtacagca agctgaccgt ggacaagagc    1260
aggtggcagc agggcaacgt gttcagctgc agcgtgatgc acgaggccct gcacaaccac    1320
tacacccaga agagcctgag cctgagcccc ggcaag                              1356
```

<210> SEQ ID NO 73
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
        115                 120
```

<210> SEQ ID NO 74
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gaggtgcagc tgctggagag cggcggcggc ctggtgcagc ccggcggcag cctgaggctg    60
agctgcgccg ccagcggctt caccttcagc tggtacgaga tgtactgggt gaggcaggcc    120
cccggcaagg gcctggagtg ggtgagcagc atcagcccca gcggcggctg gaccatgtac    180
gccgacagcg tgaagggcag gttcaccatc agcagggaca cagcaagaa caccctgtac    240 ctgcagatga acagcctgag ggccgaggac accgccgtgt actactgcgc caccccctg    300
```
tacagcagcg acggcctgag cgccggcgac atctggggcc agggcaccat ggtgaccgtg    360
agcagc    366

<210> SEQ ID NO 75
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro
                85                  90                  95

Ser Phe Gly Gln Gly Thr Arg Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
gagatcgtgc tgacccagag ccccgccacc ctgagcctga gccccggcga gagggccacc    60
ctgagctgca gggccagcca gagcgtgcac agcagctacc tggcctggta ccagcagaag    120
cccggccagg cccccaggct gctgatctac ggcgccagca gcagggccac cggcatcccc    180
gacaggttca gcggcagcgg cagcggcacc gacttcaccc tgaccatcag caggctggag    240
cccgaggact tcgccgtgta ctactgccag cagagctaca ggacccccag cttcggccag    300

```
ggcaccaggc tggagatcac caggaccgtg ccgcccccca gcgtgttcat cttcccccc       360 agcgacgagc agctgaagag cggcaccgcc agcgtggtgt gcctgctgaa caacttctac       420
cccagggagg ccaaggtgca gtggaaggtg acaacgccc tgcagagcgg caacagccag        480
gagagcgtga ccgagcagga cagcaaggac agcacctaca gcctgagcag cacccctgacc     540 ctgagcaagg ccgactacga gaagcacaag gtgtacgcct gcgaggtgac ccaccagggc       600
ctgagcagcc ccgtgaccaa gagcttcaac agggggcgagt gc                         642

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro
                85                  90                  95

Ser Phe Gly Gln Gly Thr Arg Leu Glu Ile Thr
            100                 105

<210> SEQ ID NO 78
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gagatcgtgc tgacccagag ccccgccacc ctgagcctga gccccggcga gagggccacc       60
ctgagctgca gggccagcca gagcgtgcac agcagctacc tggcctggta ccagcagaag      120
cccggccagg ccccaggct gctgatctac ggcgccagca gcagggccac cggcatcccc       180
gacaggttca gcggcagcgg cagcggcacc gacttcaccc tgaccatcag caggctggag      240
cccgaggact tcgccgtgta ctactgccag cagagctaca gaccccccag cttcggccag      300
ggcaccaggc tggagatcac c                                                321

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Tyr Glu Met Tyr
```

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ile Ser Pro Ser Gly Gly Trp Thr Met Tyr Ala Asp Ser Val Lys
1               5                   10                  15
Gly

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Pro Leu Tyr Ser Ser Asp Gly Leu Ser Ala Gly Asp Ile
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ala Ser Gln Ser Val His Ser Ser Tyr Leu Ala
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ala Ser Ser Arg Ala Thr
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gln Ser Tyr Arg Thr Pro Ser
1               5

<210> SEQ ID NO 85
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

```
                385                 390                 395                 400
Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 86
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gaagttcaat tgttagagtc tggtggcggt cttgttcagc ctggtggttc tttacgtctt      60
tcttgcgctg cttccggatt cactttctct tggtacgaga tgtattgggt tcgccaagct     120
cctggtaaag gtttggagtg gtttcttct atctctcctt ctggtggctg gactatgtat      180
gctgactccg ttaaaggtcg cttcactatc tctagagaca actctaagaa tactctctac     240
ttgcagatga acagcttaag ggctgaggac acggccgtgt attactgtgc gaccccttg      300 tatagcagtg acgggctttc ggcgggggat atctggggcc aagggacaat ggtcaccgtc     360
tcaagcgcgt cgaccaaggg cccatccgtc ttccccctgg caccctcctc caagagcacc     420
tctgggggca gcggccct gggctgcctg gtcaaggact acttcccga accggtgacg        480 gtgtcctgga actcaggcgc tctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg      780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagcccctcc cagcccccat cgagaaaacc   1020
atctccaaag ccaaagggca gccccgagaa ccacaggtct acaccctgcc cccatcccgg   1080
gaggagatga ccaagaacca ggtcagcctg acctgcctgg tcaaaggctt ctatcccagc    1140
gacatcgccg tggagtggga gagcaatggg cagccggaga caactacaa gaccacgcct     1200 cccgtgctgg actccgacgg ctccttcttc ctctatagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356

<210> SEQ ID NO 87
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
        115                 120

<210> SEQ ID NO 88
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gaagttcaat tgttagagtc tggtggcggt cttgttcagc ctggtggttc tttacgtctt    60
tcttgcgctg cttccggatt cactttctct tggtacgaga tgtattgggt cgccaagct   120 cctggtaaag gtttggagtg gtttcttct atctctcctt ctggtggctg actatgtat   180 gctgactccg ttaaaggtcg cttcactatc tctagagaca actctaagaa tactctctac   240
ttgcagatga acagcttaag ggctgaggac acggccgtgt attactgtgc gaccccttg    300 tatagcagtg acgggctttc ggcggggat atctggggcc aagggacaat ggtcaccgtc    360
tcaagc                                                              366

<210> SEQ ID NO 89
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro

```
              85                  90                  95
Ser Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 90
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
gagatcgtgc tgacccagtc tccagccacc ctctctttgt ctccagggga aagagccacc    60
ctctcctgca gggccagtca gagtgttcac agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagttta ctactgtcaa cagagttacc gcacccctts cttcggccaa   300
gggacacgac tggagattaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45
```

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Tyr Arg Thr Pro
                85                  90                  95

Ser Phe Gly Gln Gly Thr Arg Leu Glu Ile Lys
            100                 105

<210> SEQ ID NO 92
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gagatcgtgc tgacccagtc tccagccacc ctctctttgt ctccagggga aagagccacc      60
ctctcctgca gggccagtca gagtgttcac agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagttta ctactgtcaa cagagttacc gcacccctc cttcggccaa      300 gggacacgac tggagattaa a                                              321

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Tyr Glu Met Tyr
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Ile Ser Pro Ser Gly Gly Trp Thr Met Tyr Ala Asp Ser Val Lys
1               5                   10                  15

Gly

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Leu Tyr Ser Ser Asp Gly Leu Ser Ala Gly Asp Ile
1               5                   10

```
<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Gln Ser Val His Ser Ser Tyr Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ala Ser Ser Arg Ala Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Ser Tyr Arg Thr Pro Ser
1               5

<210> SEQ ID NO 99
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140
```

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 100
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaggtgcagc tgctggagag cggcggcggc ctggtgcagc ccggcggcag cctgaggctg      60
agctgcgccg ccagcggctt caccttcagc tggtacgaga tgtactgggt gaggcaggcc     120
cccggcaagg gcctggagtg ggtgagcagc atcagcccca gcggcggctg gaccatgtac     180
gccgacagcg tgaagggcag gttcaccatc agcagggaca acagcaagaa caccctgtac     240

-continued

```
ctgcagatga acagcctgag ggccgaggac accgccgtgt actactgcgc caccccctg      300 tacagcagcg acggcctgag cgccggcgac atctggggcc agggcaccat ggtgaccgtg      360
agcagcgcca gcaccaaggg ccccagcgtg ttccccctgg cccccagcag caagagcacc      420
agcggcggca ccgccgccct gggctgcctg gtgaaggact acttccccga gcccgtgacc      480
gtgagctgga acagcggcgc cctgaccagc ggcgtgcaca ccttccccgc cgtgctgcag      540
agcagcggcc tgtacagcct gagcagcgtg gtgaccgtgc cagcagcag cctgggcacc       600 cagacctaca tctgcaacgt gaaccacaag cccagcaaca ccaaggtgga caagagggtg      660
gagcccaaga gctgcgacaa gacccacacc tgccccccct gccccgcccc cgagctgctg      720
ggcggcccca gcgtgttcct gttcccccc aagcccaagg acaccctgat gatcagcagg       780
acccccgagg tgacctgcgt ggtggtggac gtgagccacg aggaccccga ggtgaagttc      840
aactggtacg tggacggcgt ggaggtgcac aacgccaaga ccaagcccag ggaggagcag      900
tacaacagca cctacagggt ggtgagcgtg ctgaccgtgc tgcaccagga ctggctgaac      960
ggcaaggagt acaagtgcaa ggtgagcaac aaggccctgc ccgcccccat cgagaagacc     1020
atcagcaagg ccaagggcca gccccaggag ccccaggtgt acaccctgcc ccccagcagg     1080
gaggagatga ccaagaacca ggtgagcctg acctgcctgg tgaagggctt ctaccccagc     1140
gacatcgccg tggagtggga gagcaacggc cagcccgaga caactacaa gaccaccccc      1200 cccgtgctgg acagcgacgg cagcttcttc ctgtacagca gctgaccgt ggacaagagc       1260 aggtggcagc agggcaacgt gttcagctgc agcgtgatgc acgaggccct gcacaaccac     1320
tacacccaga agagcctgag cctgagcccc ggcaag                                1356
```

<210> SEQ ID NO 101
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Met Tyr Trp Val Arg Gln Ala Pro Gly Lys Gly Leu Glu Trp Val
        35                  40                  45

Ser Ser Ile Ser Pro Ser Gly Gly Trp Thr Met Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Leu Tyr Ser Ser Asp Gly Leu Ser Ala Gly Asp Ile Trp
            100                 105                 110

Gly Gln Gly Thr Met Val Thr Val Ser Ser
        115                 120
```

<210> SEQ ID NO 102
<211> LENGTH: 366
<212> TYPE: DNA
<213> ORGANISM: Artificial Sequence -continued

```
<220> FEATURE:
<223> OTHER INFORMATION: Description of Artificial Sequence: Synthetic
      polynucleotide

<400> SEQUENCE: 102
gaggtgcagc tgctggagag cggcggcggc ctggtgcagc ccggcggcag cctgaggctg      60
agctgcgccg ccagcggctt caccttcagc tggtacgaga tgtactgggt gaggcaggcc     120
cccggcaagg gcctggagtg ggtgagcagc atcagcccca gcggcggctg gaccatgtac     180
gccgacagcg tgaagggcag gttcaccatc agcagggaca acagcaagaa caccctgtac     240
ctgcagatga acagcctgag ggccgaggac accgccgtgt actactgcgc cccccctg      300 tacagcagcg acggcctgag cgccggcgac atctggggcc agggcaccat ggtgaccgtg     360
agcagc                                                                366

<210> SEQ ID NO 103
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Arg Thr Pro
                85                  90                  95

Ser Phe Gly Gln Gly Thr Arg Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 104
<211> LENGTH: 642
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 104

```
gagatcgtgc tgacccagag ccccgccacc ctgagcctga gccccggcga gagggccacc      60
ctgagctgca gggccagcca gagcgtgcac agcagctacc tggcctggta ccagcagaag     120
cccggccagg cccccaggct gctgatctac ggcgccagca gcagggccac cggcatcccc     180
gacaggttca gcggcagcgg cagcggcacc gacttcaccc tgaccatcag caggctggag     240
cccgaggact cgccgtgta ctactgccag caggactaca ggaccccag cttcggccag       300
ggcaccaggc tggagatcac caggaccgtg gccgccccca gcgtgttcat cttcccccc      360
agcgacgagc agctgaagag cggcaccgcc agcgtggtgt gcctgctgaa caacttctac     420
cccagggagg ccaaggtgca gtggaaggtg acaacgccc tgcagagcgg caacagccag      480
gagagcgtga ccgagcagga cagcaaggac agcacctaca gcctgagcag caccctgacc     540
ctgagcaagg ccgactacga gaagcacaag gtgtacgcct gcgaggtgac ccaccagggc     600
ctgagcagcc ccgtgaccaa gagcttcaac agggcgagt gc                         642
```

<210> SEQ ID NO 105
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val His Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Asp Tyr Arg Thr Pro
                85                  90                  95
Ser Phe Gly Gln Gly Thr Arg Leu Glu Ile Thr
            100                 105
```

<210> SEQ ID NO 106
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
gagatcgtgc tgacccagag ccccgccacc ctgagcctga gccccggcga gagggccacc      60
ctgagctgca gggccagcca gagcgtgcac agcagctacc tggcctggta ccagcagaag     120
cccggccagg cccccaggct gctgatctac ggcgccagca gcagggccac cggcatcccc     180
gacaggttca gcggcagcgg cagcggcacc gacttcaccc tgaccatcag caggctggag     240
cccgaggact cgccgtgta ctactgccag caggactaca ggaccccag cttcggccag       300
```
ggcaccaggc tggagatcac c                                              321

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Trp Tyr Glu Met Tyr
1               5

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Ile Ser Pro Ser Gly Gly Trp Thr Met Tyr Ala Asp Ser Val Lys
1               5                   10                  15

Gly

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Leu Tyr Ser Ser Asp Gly Leu Ser Ala Gly Asp Ile
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ala Ser Gln Ser Val His Ser Ser Tyr Leu Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ala Ser Ser Arg Ala Thr
1               5

<210> SEQ ID NO 112
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 112

Gln Gln Asp Tyr Arg Thr Pro Ser
1               5

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Ala Ser Gln Ser Val Ser Ser Ser Tyr Leu Ala
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Gln Ser Val His Ser Ser Tyr Leu Ala
1               5                   10

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Gln Ser Tyr Ser Thr Pro Ser
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Ser Tyr Arg Thr Pro Ser
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Asp Tyr Ser Thr Pro Ser
1               5
```

```
<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Gln Asp Tyr Arg Thr Pro Ser
1               5

<210> SEQ ID NO 119
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
                20                  25                  30

Glu Met Tyr Trp Val Arg Gln Ala Pro Gly Lys Gly Leu Glu Trp Val
            35                  40                  45

Ser Ser Ile Ser Pro Ser Gly Gly Trp Thr Met Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr

<210> SEQ ID NO 120
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala
```

```
<210> SEQ ID NO 121
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys Gln Gln Ser Tyr Ser Thr Pro
                85                  90                  95

Ser

<210> SEQ ID NO 122
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln
                85                  90
```